(12) United States Patent
Hou et al.

(10) Patent No.: US 9,179,846 B2
(45) Date of Patent: Nov. 10, 2015

(54) METHOD AND SYSTEM FOR CHARACTERIZING CARDIAC FUNCTION BASED ON DYNAMIC IMPEDANCE

(71) Applicant: PACESETTER, INC., Sylmar, CA (US)

(72) Inventors: Wenbo Hou, Valencia, CA (US); Kritika Gupta, San Francisco, CA (US); Bruce A. Morley, Acton, CA (US); Laurence S. Sloman, West Hollywood, CA (US); Rupinder Bharmi, Canyon Country, CA (US); Xiaoyi Min, Camarillo, CA (US); Riddhi Shah, San Jose, CA (US); Gene A. Bornzin, Simi Valley, CA (US); Edward Karst, Los Angeles, CA (US)

(73) Assignee: PACESETTER, INC., Sylmar, CA (US)

( * ) Notice: Subject to any disclaimer, the term of this patent is extended or adjusted under 35 U.S.C. 154(b) by 0 days.

(21) Appl. No.: 13/841,184

(22) Filed: Mar. 15, 2013

(65) Prior Publication Data

US 2014/0276125 A1    Sep. 18, 2014

(51) Int. Cl.
| | |
|---|---|
| *A61B 5/02* | (2006.01) |
| *A61B 5/0215* | (2006.01) |
| *A61N 1/365* | (2006.01) |
| *A61B 5/00* | (2006.01) |
| *A61B 5/0402* | (2006.01) |
| *A61B 5/053* | (2006.01) |
| *A61B 5/029* | (2006.01) |
| *A61B 5/11* | (2006.01) |

(52) U.S. Cl.
CPC ......... *A61B 5/02152* (2013.01); *A61B 5/02028* (2013.01); *A61B 5/0402* (2013.01); *A61B 5/053* (2013.01); *A61B 5/0538* (2013.01); *A61B 5/4836* (2013.01); *A61B 5/686* (2013.01); *A61B 5/7246* (2013.01); *A61N 1/36585* (2013.01); *A61B 5/029* (2013.01); *A61B 5/1118* (2013.01)

(58) Field of Classification Search
CPC ............... A61B 5/0452; A61B 5/0006; A61B 5/02152; A61B 5/02028; A61B 5/4836; A61N 1/3627; A61N 1/36521; A61N 1/36585
USPC ............................................ 600/508; 607/17
See application file for complete search history.

(56) References Cited

U.S. PATENT DOCUMENTS

| | | | |
|---|---|---|---|
| 6,577,892 B2 | 6/2003 | Schomburg | |
| 7,410,467 B2 | 8/2008 | Cooper | |
| 7,751,888 B1 | 7/2010 | Schecter | |
| 8,157,848 B2 | 4/2012 | Zhang et al. | |
| 2001/0021814 A1 | 9/2001 | Schomburg | |
| 2007/0191901 A1* | 8/2007 | Schecter | 607/17 |
| 2010/0204585 A1 | 8/2010 | Zhang | |
| 2011/0257697 A1* | 10/2011 | Jarverud | 607/18 |

* cited by examiner

*Primary Examiner* — Christopher D Koharski
*Assistant Examiner* — Michael Carey

(57) ABSTRACT

A method and system are provided for characterizing cardiac function. The method and system comprise collecting cardiac signals associated with electrical or mechanical behavior of a heart over at least one cardiac cycle; identifying a timing feature of interest (FOI) from the cardiac signals; collecting dynamic impedance (DI) data over at least one cardiac cycle (CC), designated by the timing FOI, along at least one of i) a venous return (VR) vector or ii) a right ventricular function (RVF) vector; and analyzing at least one morphologic characteristic from the DI data based on at least one of i) a VR-DI correlation metric to obtain a VR indicator associated with the CC or ii) a RVF-DI correlation metric to obtain a RVF indicator associated with CC.

22 Claims, 13 Drawing Sheets
(2 of 13 Drawing Sheet(s) Filed in Color)

METHOD AND SYSTEM FOR CHARACTERIZING CARDIAC FUNCTION BASED ON DYNAMIC IMPEDANCE

FIELD OF THE INVENTION

Embodiments of the present invention generally relate to characterizing cardiac function, and more particularly to methods and systems that utilize dynamic impedance as indicators of cardiac function.

BACKGROUND OF THE INVENTION

Today, pacemaker configuration is often performed by selecting a desired lead location for a specific patient (e.g., septal vs. Apical) and then programming the parameters of the pacemaker, such as the AV and/or VV delay, the rate responsive AV and/or VV delay and the like. Today, cardiac resynchronization therapy (CRT) configuration is similarly performed by selecting a desired lead location (e.g., by avoiding infarct zones, reduced dyssynchrony, LV apical vs. septal) and then programming the CRT device with desired AV and VV delays. The AV and VV delays are selected traditionally by physicians through the use of an echocardiographic evaluation method. However, a comprehensive echocardiographic evaluation is time consuming and has high variations.

In addition, device manufacturers have implemented algorithms within implanted medical devices that select AV and VV delays based on intra-cardiac electrograms (IEGM). For example, one device-based method uses P wave duration to estimate intra-atrial conduction time for setting the timing of ventricular (V) pacing. This device-based method is intended to achieve similar effects as an echocardiography evaluation based method, namely to improve atrial-filling behavior. However, device-based methods that utilize the P wave, as detected in the RA, represent a rough estimation of intra-atrial conduction (IACT). As such, the potential exists that the P wave estimate may be an inaccurate estimate of IACT.

Thus, these conventional selection methods currently utilize timing features (conduction delay, dyssynchrony measures), systemic hemodynamic measures (Stroke volume, pre-load) and echocardiography evaluation bases measures of cardiac function for determining ejection time, myocardial performance index, left ventricular end systole volume, and left ventricular end diastole volume.

However, it is preferred to tailor each device to the individual patient's underlying etiology and functional status. Yet, a comprehensive echocardiography evaluation assessment is time consuming. Also, when the parameters of a pacemaker are set to a preferred setting, while a patient is in the clinic, the same parameter settings may not reflect the best parameter settings for the patient when the person is ambulatory and active.

SUMMARY

In accordance with embodiments herein, a method and system are provided for characterizing cardiac function. The method comprises collecting cardiac signals associated with electrical or mechanical behavior of a heart over at least one cardiac cycle; identifying a timing feature of interest (FOI) from the cardiac signals; collecting dynamic impedance (DI) data over at least one cardiac cycle (CC), designated by the timing FOI, along at least one of i) a venous return (VR) vector or ii) a right ventricular function (RVF) vector; and analyzing at least one morphologic characteristic from the DI data based on at least one of i) a VR-DI correlation metric to obtain a VR indicator associated with the CC or ii) a RVF-DI correlation metric to obtain a RVF indicator associated with CC.

Optionally, the method may comprise, over multiple cardiac cycles, modulating at least one IMD therapy parameter and repeating the collecting and identifying operations to obtain a collection of at least one of VR indicators or RVF indicators associated with different IMD therapy parameters. Optionally, the method may further comprise adjusting an IMD therapy configuration based on at least one of i) the collection of VR indicators and the VR-DI correlation metric such that the IMD operates to encourage a select VR level or ii) the collection of RVF indicators and the RVF-DI correlation metric such that the IMD operates to encourage a select RVF level.

The method may determine a select level for the at least one IMD therapy parameter that provides at least one of i) a select peak to peak amplitude, ii) a select minimum amplitude, iii) a select DI change per unit time (dZ/dt) or iv) a select slope, of the DI data when plotted over time. The collecting operation may utilize an IMD case electrode and at least one of an SVC electrode, an IVC electrode and an RA electrode to define the VR vector and to collect the DI data. The analyzing operation may include determining, as the morphologic characteristic, at least one of i) a peak to peak (P-P) amplitude, ii) a minimum amplitude, iii) a minimum DI change per unit time (dZ/dt) or iv) slope, of the DI data over the CC.

In accordance with an embodiment, the VR-DI correlation metric represents a correlation between a mean pulmonary arterial pressure (mean PAP) and at least one of i) the P-P amplitude, ii) the minimum amplitude or iii) the dZ/dt. Optionally, the VR-DI correlation metric represents at least one of i) a relation between changes in the P-P amplitude and changes in stroke volume and contractile strength, and ii) a relation between changes in the slope of the DI data and changes in direction and degree of cardiac contractility.

Optionally, the method may further comprise aligning the VR vector such that changes in the DI data substantially correlate with changes in stroke volume, end ventricular diastolic pressure, and mean pulmonary arterial pressure (mean PAP) for at least a portion of a duration of fluid loading and unloading. The VR vector may extend through at least one of the SVC, RA or IVC. The DI data may be collected and analyzed in connection with a select activity state and a select posture position of a patient.

In accordance with an embodiment herein, a system is provided for characterizing cardiac function. The system comprises inputs configured to collect cardiac signals associated with electrical or mechanical behavior of a heart over at least one cardiac cycle (CC); and a CS module configured to identify a timing feature of interest (FOI) from the cardiac signals. The system further comprises a DI module configured to collect dynamic impedance (DI) data over at least one cardiac cycle (CC), designated by the timing FOI, along at least one of i) a venous return (VR) vector or ii) a right ventricular function (RVF) vector and a morphology characteristic (MC) module configured to analyze at least one morphologic characteristic from the DI data based on at least one of i) a VR-DI correlation metric to obtain a VR indicator associated with the CC or ii) a RVF-DI correlation metric to obtain a RVF indicator associated with CC.

Optionally, the system may further comprise a therapy module configured to modulate, over multiple cardiac cycles, at least one therapy parameter while the system obtains a collection of at least one of VR indicators or RVF indicators associated with different therapy parameters. The therapy module may be configured to adjust an therapy configuration based on at least one of i) the collection of VR indicators and the VR-DI correlation metric such that the system operates to encourage a select VR level or ii) the collection of RVF indicators and the RVF-DI correlation metric such that the system operates to encourage a select RVF level.

Optionally, the MC module may be further configured to determine a select level for the at least one therapy parameter that provides at least one of i) a select peak to peak amplitude, ii) a select minimum amplitude, iii) a select DI change per unit time (dZ/dt), iv) a select slope, v) a select ventricular filling time, or vi) a select ventricular emptying time, of the DI data when plotted over time. The MC module may be configured to determine, as the morphologic characteristic, at least one of i) a peak to peak (P-P) amplitude, ii) a minimum amplitude, iii) a minimum DI change per unit time (dZ/dt), iv) slope, v) a select ventricular filling time, or vi) a select ventricular emptying time, of the DI data over the CC. The MC module may collect and analyze the DI data in connection with a select activity state and a select posture position of a patient.

Optionally, the inputs may be configured to collect the DI data utilizing an IMD case electrode and at least one of an SVC electrode, an IVC electrode and an RA electrode to define the VR vector.

Optionally, the VR-DI correlation metric represents a correlation between a mean pulmonary arterial pressure (mean PAP) and at least one of i) the P-P amplitude, ii) the minimum amplitude or iii) the dZ/dt. The VR-DI correlation metric may represent at least one of i) a relation between changes in the P-P amplitude and changes in stroke volume and contractile strength, and ii) a relation between changes in the slope of the DI data and changes in direction and degree of cardiac contractility.

The VR vector may be aligned such that changes in the DI data substantially correlate with changes in stroke volume, end ventricular diastolic pressure, and mean pulmonary arterial pressure (mean PAP) for at least a portion of a duration of fluid loading and unloading.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION

Figure 1A:
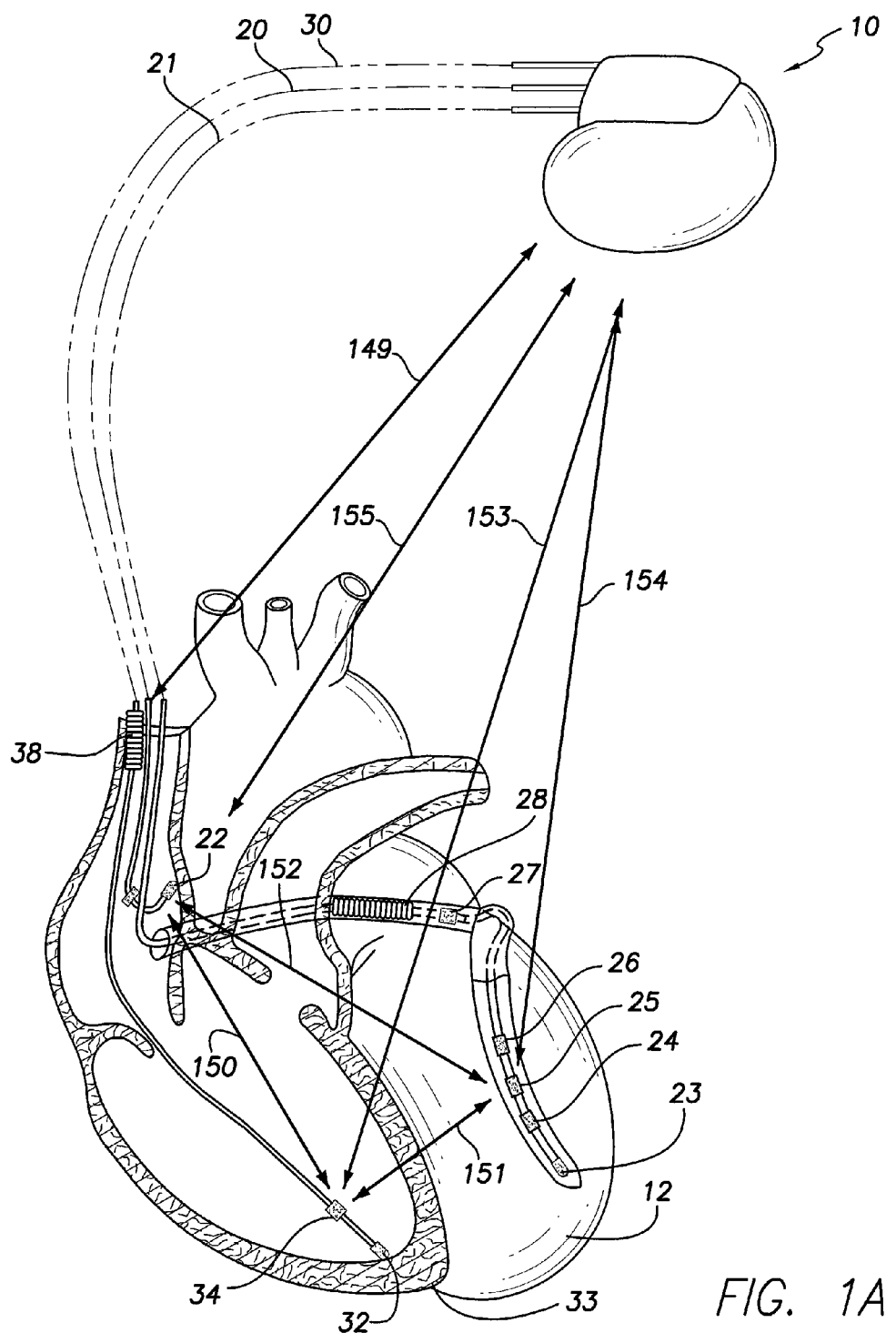
FIG. 1A illustrates a simplified diagram of an implantable medical IMD in electrical communication with leads implanted in or proximate a patient's heart in accordance with an embodiment.

In accordance with embodiments herein, methods and systems are described to characterize the systemic and cardiac function of a patient on a beat-by-beat basis. A series of studies in canines were conducted to characterize the effect of hemodynamics on dynamic impedance as recorded from various anode cathode electrode combinations (using transvenous implanted leads). An analysis of the canine data has helped to provide a means of better identifying correlation between dynamic impedance and chamber dynamics (e.g., filling, emptying, timing). Embodiments herein are described for characterizing cardiac functions, such as venous return, right ventricular emptying and filling and the like.

Embodiments are also described for setting parameters to improve atrial filling, ventricular emptying, venous return, systolic time and the like, depending on a patient's specific need. For example, embodiments utilize dynamic impedance (DI) data collected along one or more vectors associated with certain cardiac functions such as venous return (VR) or right ventricular function (RVF). For example, a VR vector may be defined by delivering current between an SVC-coil electrode and a case electrode, while measuring a voltage potential between the same or a different SVC-coil electrode and the case electrode. An RVF vector may be defined by delivering current (and measuring voltage potential) between an RV tip, coil or ring electrode and an IMD case electrode. Specific morphological metrics may be associated with DI data collected along the VR vector or the RVF vector, where the morphological metrics enable the DI data to be used to characterize a status of the patient's venous return or right ventricular function.

In general, venous return constitutes the flow of blood back to the heart. Under steady state conditions, venous return equals cardiac output when averaged over time because the cardiovascular system is essentially a closed loop. Although cardiac output (CO) and venous return are interdependent, CO and VR can be independently regulated. Venous return is influenced by various factors such as muscle contraction, decreased venous compliance, respiratory activity, vena cava compression and gravity. For example, when muscle contraction increases, VR transiently increases, while VR peripherally decreases. When venous compliance decreases, VR becomes harder to control. In connection with respiratory activity, during inspiration, VR becomes partially inhibited; whereas during expiration, VR increases. When the vena cava compression increases or when gravity increases, then venous return decreases. As the VR changes, the methods and systems herein identify the VR changes and undertake a process to identify a new IMD therapy configuration that is intended to encourage a select or desired VR level or range.

Embodiments herein are described in which a VR related dynamic impedance vector (SVCcoil-case) is used to track the venous return on a continual basis. Based on the underlying reason for a change in venous return, the IMD programming may be changed (manually or automatically) to provide a select level of hemodynamic support. For example, a dynamic impedance based method for identifying a select level of venous return when preload is not varying or varied by a small amount. The dynamic impedance (DI) data recorded from the VR vector is used to determine venous return using one or more morphology characteristics from the DI data.

FIG. 1A illustrates a simplified diagram of an implantable medical IMD 10 in electrical communication with three leads 20, 21 and 30 implanted in or proximate a patient's heart 12 for delivering single or multi-chamber stimulation (e.g. pacing, ATP therapy, high voltage shocks and the like) and for characterizing cardiac function according to an embodiment. The stimulation may include pacing pulses that are delivered along one or more pacing vectors. Optionally, the stimulation may include ATP pulses or a high voltage shock that is delivered along one or more ATP therapy vectors, cardioverter vectors or defibrillation vectors. The implantable medical IMD 10 may be a pacing device, a pacing apparatus, a cardiac rhythm management device, an implantable cardiac stimulation device, an implantable cardioverter/defibrillator (ICD), a cardiac resynchronization therapy (CRT) device, a monitoring device and the like. The IMD 10 is programmable, by an operator, to set certain operating parameters, as well as therapy-related parameters. The IMD 10 is configured to operate with various configurations of leads. The IMD 10 is configured to sense various types of information and deliver various types of therapies. For example, the IMD 10 may sense intracardiac electrogram signals, impedances and the like.

In FIG. 1A, the IMD 10 is coupled to an RA lead 20 having at least an atrial tip electrode 22, which typically is implanted in the patient's right atrial appendage. The IMD 10 is coupled to an LV lead 21 that includes various electrodes, such as an LV tip electrode 23, intermediate LV electrodes 24-26, and LA electrodes 27-28. The LV lead 21 may sense atrial and ventricular cardiac signals and impedances and deliver left ventricular therapy using the LV tip electrode 23, the intermediate LV electrodes 24-26, and the LA electrodes 27 and 28. Left atrial therapy uses, for example, first and second LA electrodes 27 and 28. The LV and LA electrodes 23-28 may be used as sensing sites, where cardiac signals and/or impedances are sensed, and/or may be used as pacing and/or shock therapy sites. A right ventricular lead 30 may include one or more of an RV tip electrode 32, an RV ring electrode 34, and a superior vena cava (SVC) coil electrode 38 (also known as a RA coil electrode). The right ventricular lead 30 is capable of sensing cardiac signals and/or impedances, and delivering stimulation in the form of pacing and shock therapy to the SVC and/or right ventricle.

Optionally, more or fewer electrodes may be utilized. The LV electrodes may be separated further apart or positioned closer to one another. Optionally, all or a portion of the LV electrodes may be shifted along the LV lead 21 until positioned proximate to the mitral valve, aortic valve, or the left atrial ports to/from the pulmonary veins. The LV lead 21 may be inserted directed into the LV chamber or inserted into a vein or artery extending along the heart wall proximate to the left ventricle. Optionally, the LV lead 21 may be coupled to a patch or mesh net electrode that is secured to or located adjacent to an exterior wall of the left ventricle and/or the left atrium.

Embodiments are described herein, whereby multiple electrodes are utilized to sense impedance along multiple sensing vectors in order to measure local impedance information along the select sensing vectors. Impedance measurements collected along the select sensing vectors are utilized to derive dynamic impedance data correlated to one or more cardiac functions.

The IMD 10 defines sensing vectors between various combinations of two or more electrodes 22-28, 32, 34 and 38, and the housing of the IMD 10. FIG. 1A illustrates examples of sensing vectors 149-155. The IMD 10 obtains one or more impedance measurements along the select one or more sensing vectors 149-155 which extend through a substantial majority of the portion of the heart or vessels of interest. An individual measured impedance represents the impedance of the walls of the heart 12, the blood in the heart 12 and any external tissue or muscle through which the corresponding active sensing vector extends.

The sensing vector 149 extends between the SVC coil electrode 38 and the CAN electrode of the IMD 10. The sensing vector 150 extends between the RA electrode 22 and the RV electrode 34. The sensing vector 151 extends between the RV electrode 34 and the LV electrode 25. The sensing vector 152 extends between the LV electrode 25 and the RA electrode 22. The sensing vector 153 extends between the RV electrode 34 and the CAN electrode of the IMD 10. The sensing vector 154 extends between the LV electrode 25 and the CAN electrode. The sensing vector 155 extends between the RA electrode 22 and the CAN. Optionally, alternative and/or additional electrodes may be used to form alternative and/or additional sensing vectors.

Each LV and RV electrode 22-38 represents a potential sensing site and/or therapy site. When functioning as a sensing site, the corresponding LV and/or RV electrode sense signals that are utilized to obtain impedance measurements. The sensing sites differ based on the type of device and type of detection algorithm utilized.

For example, in a CRT-D type device, when utilizing the PE algorithm, the device utilizes sensing vectors that extend between the RV coil electrode and CAN, and between a LV ring electrode and the CAN. In an ICD type device, when utilizing the PE algorithm, the device utilizes sensing vectors that extend between the RV coil electrode and the CAN and between the RV ring electrode and the CAN. In a CRT-P type device, when utilizing the PE algorithm, the device utilizes sensing vectors that extend between the LV ring electrode and the CAN, between the RA ring electrode and the CAN, and between the RV ring electrode and CAN. In a pacemaker type device, the device generally utilizes an active sensing vector that extends between the RV ring electrode and the CAN.

The impedance measured along the sensing vectors 149-155 may be expressed in terms of ohms. Alternatively, the impedance may be expressed as an admittance measurement. The admittance may be inversely related to the impedance. The impedance measured along the sensing vectors 149-155 may vary based on a variety of factors, including the amount of fluid in one or more chambers of the heart 12 and/or thoracic space. As a result, the impedance measurement may be indicative of LAP. As more blood fills the left atrium and pulmonary veins, the LAP increases. Blood is more electrically conductive than the myocardium of the heart 12. Consequently, as the amount of blood in the left atrium increases, the LAP increases and the impedance measured along the active sensing vector decreases. Conversely, decreasing LAP may result in the impedance measurement increasing as there is less blood in the left atrium and pulmonary veins.

Optionally, impedance measurements along various sensing vectors may be utilized to monitor and characterize pressure and blood flow in other chambers of the heart, such as RA, RV, LA and/or LV pressure and blood flow.

Figure 1B:
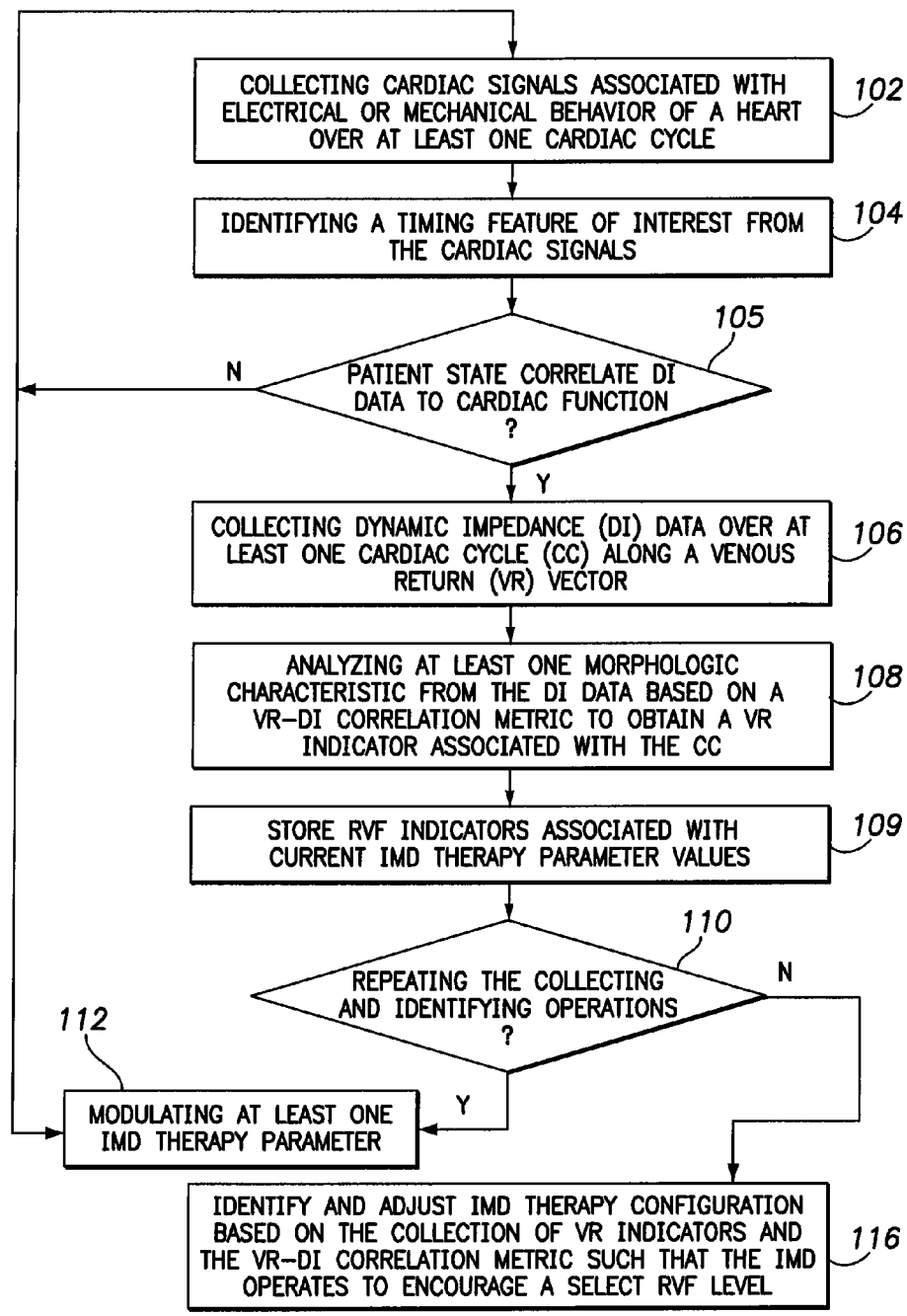
FIG. 1B illustrates a venous return cardiac function characterization method to be carried out in accordance with an embodiment by one or more of an IMD, external programmer and system described herein.

FIG. 1B illustrates a cardiac function characterization method 100 to be carried out in accordance with an embodiment by one or more of an IMD, external programmer and system described herein. The method of FIG. 1B begins with the therapy parameters of the IMD 10 set to predetermined values and/or set manually, or automatically by the IMD, based on conventional programming techniques. The IMD therapy parameters may include one or more of AV delay, VV delay, pacing electrode combination, stimulus pulse width, strength, interval and the like.

Beginning at 102, the method collects cardiac signals associated with electrical and/or mechanical behavior of a heart over at least one cardiac cycle while an IMD operates based on current IMD therapy parameter values. For example, the cardiac signals may be intra-cardiac electrogram (IEGM) signals, EKG signals, and the like. The cardiac signals may be collected from external skin electrodes, the implanted electrodes 22-38 (along one or more of sensing vectors 149-155) and the like. The cardiac signals may be indicative of mechanical behavior, such as from an accelerometer or other sensor that determines an amount of activity and/or an orientation of the patient. The cardiac signals may indicate mechanical behavior such as exercise, climbing stairs, walking, laying in a prone or supine position, sitting up-right, standing, and the like.

At 104, the method identifies a timing feature of interest (FOI) from the cardiac signals. For example, the timing feature of interest may be the peak of the R-wave, the start or center of the P-wave, the ST segment, and the like. The timing feature may be intrinsic (e.g., a naturally occurring cardiac event) or paced (e.g., a paced R-wave, a paced P-wave, etc.). When the cardiac signal is indicative of mechanical behavior, the timing feature of interest may represent the amount of movement (indicative of exercise), the orientation of the patient with respect to gravity (prone, supine, standing, etc.) and the like.

At 105, the method utilizes the timing FOI to determine whether the patient is in a state in which dynamic impedance data, if acquired, would substantially correlate to the cardiac function of interest. For example, the method may utilize the cardiac signals to identify an arrhythmia, determine the heart rate, determine a starting point for a cardiac cycle, and the like. When the cardiac signal is indicative of mechanical behavior, the timing feature of interest may be used to determine an exertion level or patient orientation. The patient state may be used to determine whether to perform subsequent DI data collection and analysis. For example, when the patient state indicates that the patient is experiencing an excessively high heart rate, flow may return to 102 and/or the method may determine to cease operation for a period of time or a predetermined number of cardiac cycles. As explained herein, when the patient is undergoing heavy excursion, the DI data may not substantially track certain cardiac functions as closely as desired. The degree to which DI data is expected to track or correlate to a cardiac function of interest (CFI) may be characterized in terms of variance, deviation and the like. As an example, the method may use, at 105, predetermined, select or automatically updated, thresholds for one or more timing features of interest. When the measured cardiac signal exceeds (or falls below) a threshold, the method may determine at 105 that too much variance exists between DI data and the CFI for present patient state.

Alternatively, at 105 when the patient state indicates that the DI data should correlate to cardiac function, then flow moves to 106.

At 106, the method collects dynamic impedance (DI) data for a collection window over at least one cardiac cycle (CC) along at least one vector of interest, such as a venous return (VR) vector. The VR vector may be aligned such that changes in the DI data substantially correlate with changes in CFI, such as stroke volume, end ventricular diastolic pressure, and/or mean pulmonary arterial pressure (mean PAP) for at least a portion of the duration of fluid loading and unloading. For example, the VR vector may extend through at least one of the SVC, RA or IVC. For example, the collecting operation may collect the DI data along a VR vector that is defined by an IMD case electrode and at least one of an SVC electrode, an IVC electrode and an RA electrode. The select combination of electrodes that defines the VR vector are used to collect the DI data. Optionally, different electrode combinations may be used to collect subsets of the DI data, where each subset of DI data may be analyzed for a common, or for different, morphologic characteristics, where the subsets of DI data collectively track the CFI.

Current flux density at the surface of the SVC electrode (e.g., or IVC electrode or RA electrode) is relatively high as compared to the current flux density remote from the SVC electrode (e.g., at other chambers of the heart or outside of the heart or at the case electrode). Due to the substantially larger current flux density immediately adjacent the SVC electrode, the DI data is primarily affected by changes in the impedance in the area (e.g., the blood) immediately surrounding the SVC electrode, while changes in the impedance in areas more remote from the SVC electrode have less relative impact on changes in the dynamic impedance.

As one example, the dynamic impedance data may be recorded from an anode-cathode combination that delivers a reference current between a SVCcoil electrode and a case electrode, while measuring voltage between the same or different SVCcoil and case electrodes.

Figure 2A:
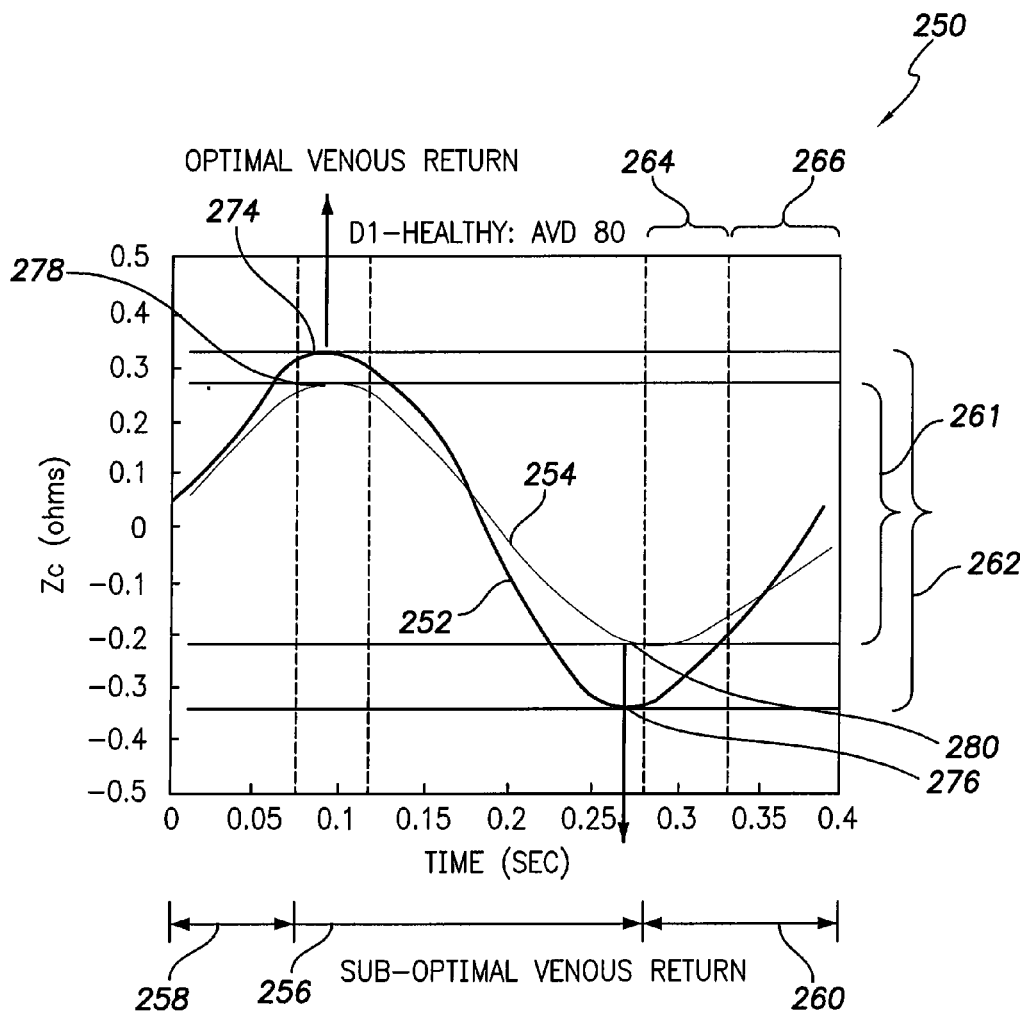
FIG. 2A illustrates a graph plotting examples of DI morphologies for different stroke volumes in accordance with an embodiment.

FIG. 2A illustrates a graph 250 plotting examples of DI morphologies 252 and 254 for patients having different stroke volumes. The graph 250 plots time along the horizontal axis and dynamic impedance along the vertical axis. The y-axis corresponds to impedance in Ohms. The y-axis includes a zero level and extends +/−1 ohm. It should be recognized that FIG. 1B is an example of the dynamic component of the measured impedance. The impedance measurement will also have a DC component that is subtracted from graph 250. The DI data has been normalized after subtracting the DC bias component such that the resultant or filtered DI data varies between +1 and −1. Hence, graph 250 shows the DI data after the DC component is subtracted and the DI data is normalized.

The x-axis extends over a 400 ms period representing one cardiac cycle. The 0 ms point represents the V pace marker at which a paced event occurred and is used as the cardiac feature of interest to form the start of a DI data collection window. Certain cardiac time zones of interest are identified along the x-axis. The cardiac cycle includes a ventricular systole period 256 and a ventricular diastole period (collectively represented by 258 and 260). The portion of the ventricular diastole period at 258 represents an active filling zone. The portion of the ventricular diastole period at 260 includes a passive filling zone 264 and an active filling zone 266.

The DI vector morphologies 252 and 254 are used to characterize venous return by applying one or more VR-DI correlation metrics to the DI data collected along one or more VR vectors. The plots of FIG. 2A illustrate DI morphologies 252 and 254, both associated with a paced heart rate of 150 bpm. The DI morphology 252 includes DI data collected while the IMD therapy parameters were set with an AV delay of 80 ms. The VR-DI correlation 254 includes DI data collected while the IMD therapy parameters were set with an AV delay of 25 ms. The DI morphology 252 corresponds to a higher amplitude venous return, while the DI morphology 254 corresponds to a lower amplitude venous return.

During systole, blood accumulates in the SVC and right atrium. As the blood accumulates, this additional blood increases the dimensions of the SVC and right atrium. As the blood from venous return accumulates in the SVC and right atrium, the impedance sensed along a VR vector decreased because the VR vector extends through more liquid and less tissue. Blood is more conductive than tissue, which lowers the impedance between the electrodes that define the VR vector.

During the ventricular diastole, the blood drains from the vena cava to the right atrium and into the right ventricle. As the blood drains from the vena cava through the RA to the RV, the volume of blood in the venous region along the VR vector decreases, thereby causing the impedance sensed by the VR vector electrodes to increase.

The DI morphologies 252 and 254 exhibit various characteristics of interest that are indicative of cardiac function of interest when VR-DI correlation metrics are applied. For example, one VR-DI correlation metric is the peak to peak amplitude. The DI morphologies 252 and 254 have peak to peak amplitudes 262 and 261, respectively. Changes in the peak to peak amplitude 262 of the impedance signal directly correlates to stroke volume (SV) and VR.

The DI morphology 252 exhibits a larger peak to peak amplitude 262 in the DI data as compared to the peak to peak amplitude 261 of the VR-DI correlation 254. In general, it is desirable for the DI data to exhibit a larger peak to peak amplitude as this is an indication of larger venous return volume. When the peak to peak amplitude increases this is indicative of an increase in venous return volume and higher SV.

Another VR-DI correlation metric is the derivative or slope of the DI morphology during the negative or down stroke of the DI data, referred to a dZ/dt. The derivative (or slope) of the down-stroke of the impedance signal forming the DI morphologies 252 and 254 are indicative of, and directly correlate to, the cardiac contractility strength. When the derivative or slope increases, this is indicative of an increase in contractility strength. When the derivative or slope decreases, this is an indication of a decrease in cardiac contractility strength. Similarly, when the derivative/slope of the VR-DI morphologies 252 or 254 increases, this is an indication of an increase in cardiac contractility.

In certain patients, other indicators of cardiac function may offset or out-weight the benefit of setting the IMD parameters to facilitate the largest potential venous return volume. For example, a patient's physiologic state may exhibit an unduly high pulmonary arterial pressure (PAP) at elevated VR volumes. When a patient exhibits unduly high PAP, it may be beneficial to target a lower VR volume (and associated peak to peak amplitude in DI data) that is also associated with a desired or select PAP level.

Figure 2B:
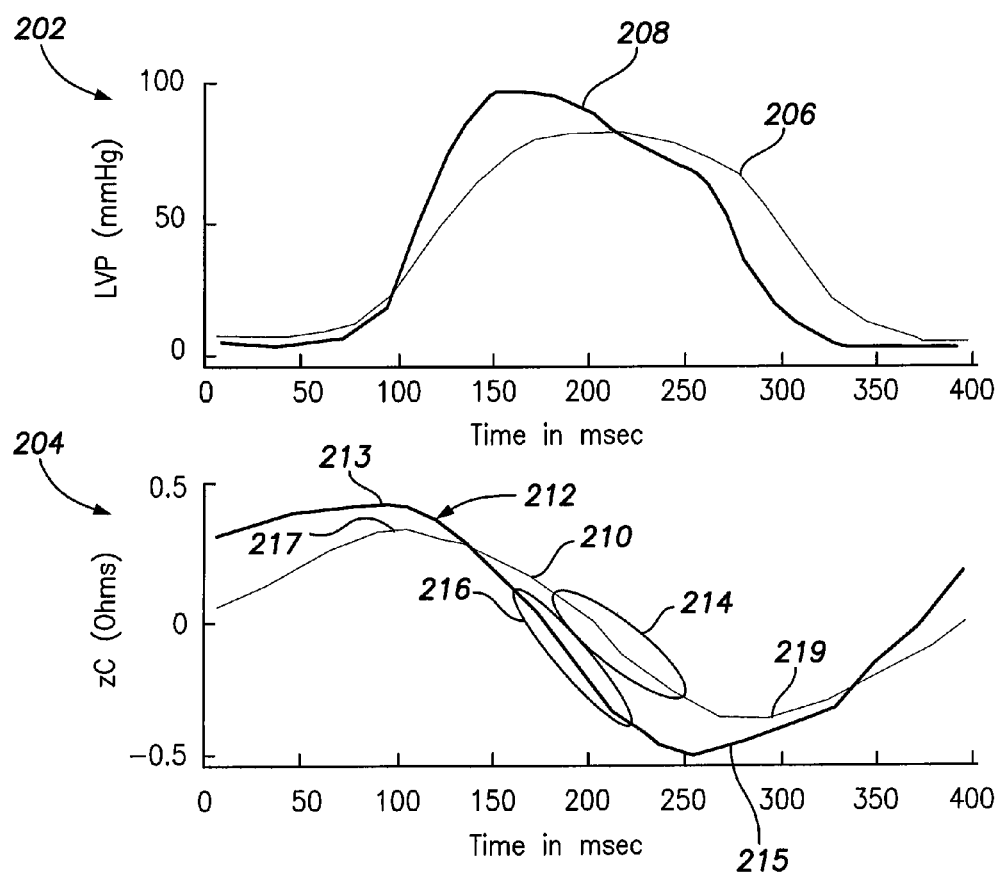
FIG. 2B illustrates graphs associated with different contractile states in accordance with an embodiment.

FIG. 2B illustrates graphs 202 and 204 exhibiting different contractile states. The DI data in graphs 202 and 204 were collected during canine experiments. During the canine experiments, a Konigsberg™ pressure sensor and Millar™ catheter were placed in the left ventricle and pulmonary artery. A Transonic™ flow probe was placed over the ascending aorta. Hemodynamic and dynamic impedance data were recorded using biventricular pacing at 150 bpm and an AV delay of 80 ms. The pacing and data collection were done while infusing the canine with Hetastarch. Post hoc analysis was conducted to compare the trends in mean pulmonary arterial pressure vs dynamic impedance features. Dynamic impedance features were derived from four (4) different vectors, which are set forth in Table 1 below.

The graph 202 plots left ventricular pressure (LVP) along the vertical axis and time along the horizontal axis associated with a single cardiac cycle. The graph 202 includes an LVP morphology 206 that exhibits normal contractile strength and an LVP morphology 208 that exhibits high contractile strength. The graph 204 plots dynamic impedance along the vertical axis and time along the horizontal axis for the same single cardiac cycle as in graph 202. The DI morphology 210 is associated with the LVP morphology 206, while the DI morphology 212 is associated with the LVP morphology 208. The DI morphology 210 correlates to normal contractile strength, while the DI morphology 212 correlates to high contractile strength. The derivative or slope of the down stroke of the DI data (also referred to as the impedance signal) is representative of the contractility. The down stroke portion 214 of the DI morphology 210 has a lower (less steep) slope or derivative than the slope/derivative of the down stroke portion 216 of the DI morphology 212 and thus DI morphology 210 correlates to lower contractility as compared to DI morphology 212.

The DI data from the DI morphologies 210 and 212 were collected along at least one. VR vector. As shown in FIG. 2B, the DI data collected along the VR vector also tracks or correlates to the morphology of the pulmonary arterial pressure. When compared to other non-VR vectors (e.g., the RVcoil to case vector), the VR vector was found to substantially correlate (e.g., be very sensitive and specific) to PAP.

Figure 3:
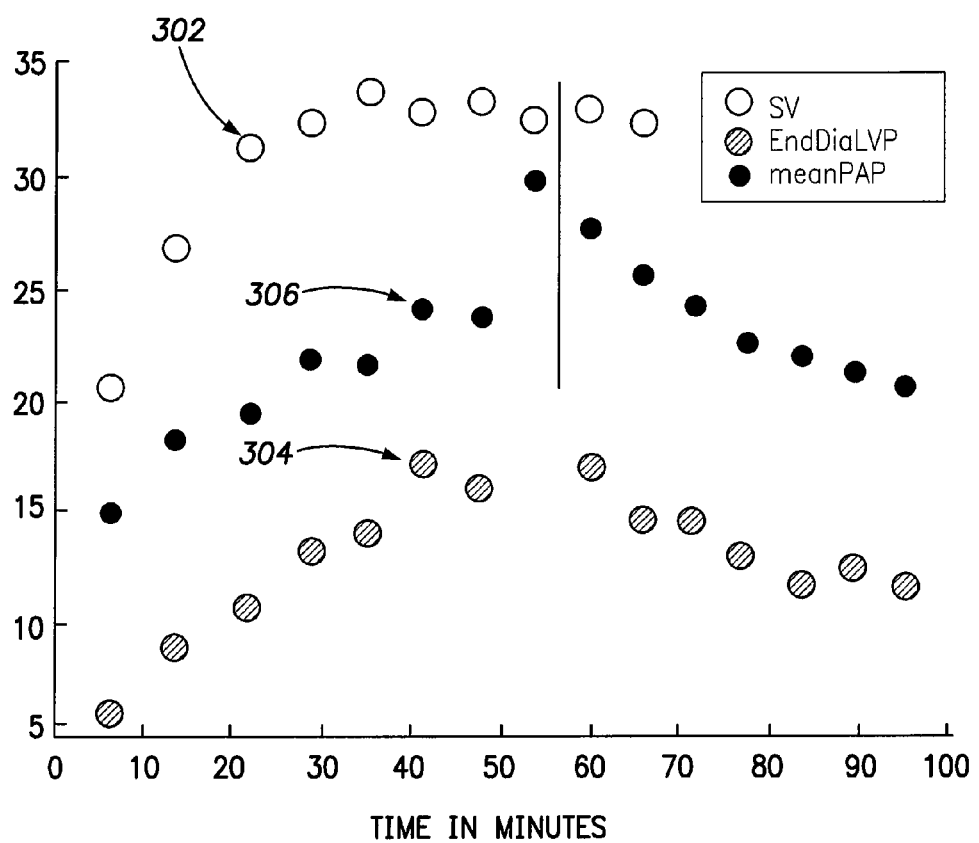
FIG. 3 plots a trend of stroke volume (SV), a trend in end diastolic pressure (EDP) and a trend in mean PAP for the duration of fluid loading and unloading.

FIG. 3 illustrates a plot showing a trend of stroke volume 302, a trend in end diastolic pressure (EDP) 304 and a trend in mean PAP 306 for the duration of fluid loading and unloading. The horizontal axis represents time. As the volume of the venous reservoir increases, the central venous pressure similarly increases which adds preload to the RV. As the RV preload increases, the EDP 304 also increases, which in turn increases stroke volume 302 primarily according to Starling's Law. In the example of FIG. 3, the stroke volume 302 flattens out at about 30 minutes because, in this example, stroke volume 302 has peaked at about 33 ml. The increase in mean PAP 306 is i) in part due to the rise in left atrial pressure that is transmitted through the pulmonary circulation beds (both venous and arterial) of the lungs and, ii) in part from an increase in stroke volume 302. While not illustrated, central venous pressure increases and pulmonary venous pressure increases with volume loading. Consequently, the right atrial and left atrial pressures increase, respectively, with the increases in central venous pressure and pulmonary venous pressure. The superior vena cave and pulmonary veins become engorged and distended and increase in diameter. The increase in diameter of the SVC causes the peak to peak modulation of the DI data measured over the SVC to case VR vector to decrease. The mean PAP was calculated as an average PAP signal over the cardiac cycle for several beats.

Table 1 below shows correlation coefficients that were calculated between mean PAP and dynamic impedance features for multiple subjects (canine) and then averaged across all subjects. Data were collected from four canine for Table 1 and FIG. 3. Table 1 illustrates in column 1, the vectors used to collect the DI data, namely the 1) SVC coil electrode to the case electrode; 2) SVC coil electrode to RV coil electrode; 3)

RA tip electrode to case electrode; and 4) RV coil electrode to case electrode. DI data were collected along each of the vectors listed in Table 1. The DI data were then analyzed for select DI features, namely the peak to peak amplitude impedance change (dZ), the minimum impedance (MinZ), and the minimum derivative, slope or rate of change in impedance (dZ/dt). These select DI features were then correlated to the mean PAP over the same cardiac cycles. The DI data from the 4 canine show that the three select DI features (Delta Z, MinZ and min dZ/dt) closely correlate with mean PAP for the vector between the SVC coil and case electrodes. In particular, the correlation between the mean PAP and the DI data collected along the SVC coil-case vector was >0.85 across all canines. The mean PAP and the DI data collected along the other three vectors SVC coil-Case vectors did not correlate as closely. The mean PAP to DI data collected along the RAtip electrode to case electrode vector exhibited only −0.26+−0.43 correlation for the peak to peak amplitude change in impedance; 0.24+−0.54 correlation for the minimum impedance and 0.44+−0.35 correlation for the minimum dZ/dt.

TABLE 1

| Pearson correlation | Delta Z | Min Z | min dZ/dt |
|---|---|---|---|
| SVC coil-Can | −0.87 ± 0.07 | 0.88 ± 0.08 | 0.85 ± 0.12 |
| SVCcoil-RVcoil | 0.32 ± 0.32 | −0.16 ± 0.66 | −0.06 ± 0.66 |
| RA tip-Can | −0.26 ± 0.43 | 0.24 ± 0.54 | 0.44 ± 0.35 |
| RV coil-Can | −0.03 ± 0.29 | 0.07 ± 0.46 | 0.07 ± 0.28 |

As shown in Table 1, trends in impedance features when correlated with mean PAP over a period of 120 minutes showed strong correlation of the SVCcoil-Case vector features with mean PAP for all 4 subjects. It is expected that a combination of features within the DI data collected along the SVCcoil-Case vector can be used to determine a selected (e.g., optimum) venous return for a given patient and for a specific activity state.

Figure 4:
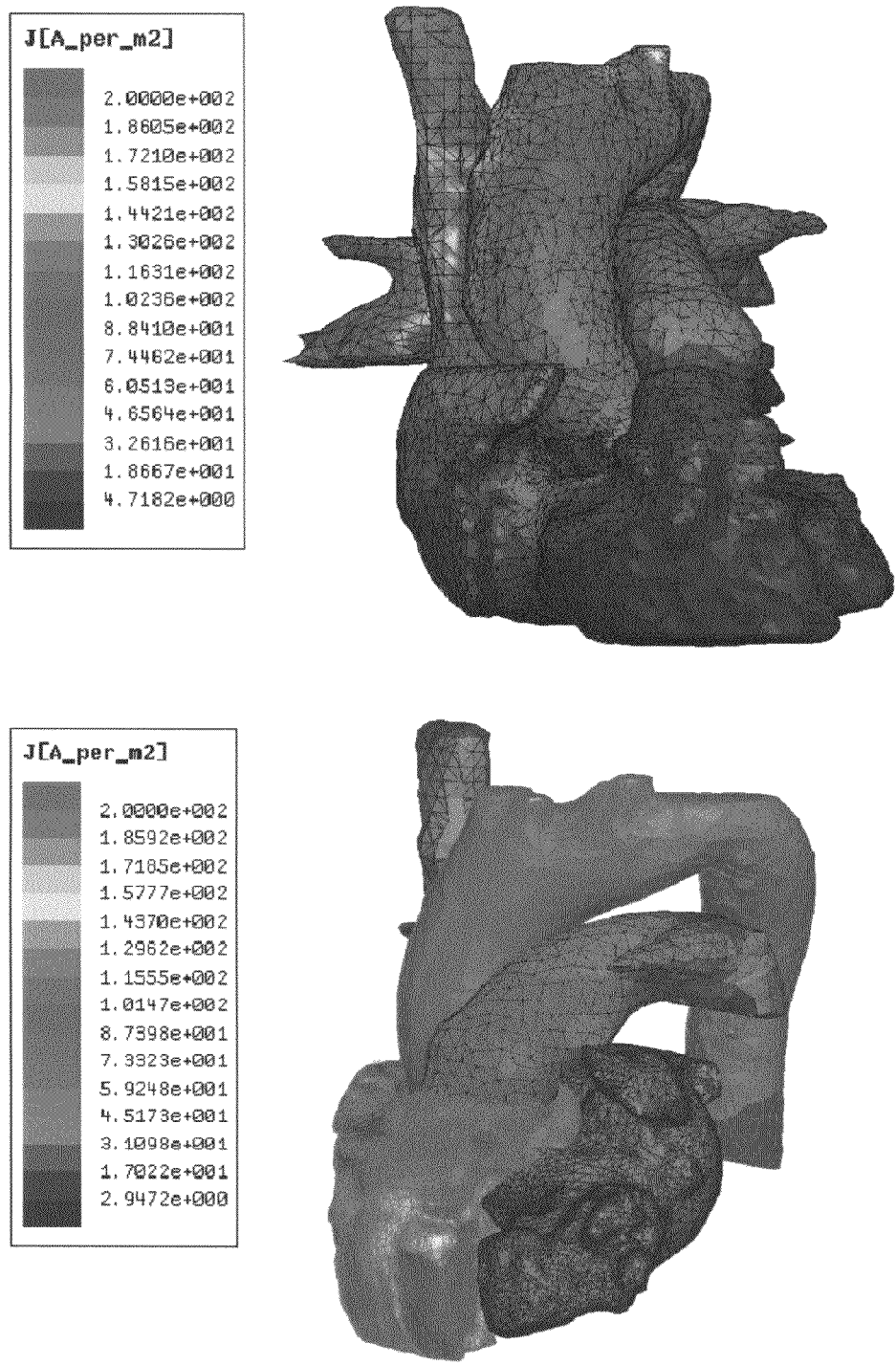
FIG. 4 illustrates computer models that were generated based on lead field theory in accordance with an embodiment.

FIG. 4 illustrates computer models 402 and 404 that were generated based on lead field theory. The models 402 and 404 show that DI data collected along a VR vector is largely affected by the blood in the superior vena cava. FIG. 4 illustrates a human heart model showing concentration of power dissipated during peak systolic phase of the cardiac cycle. FIG. 4 shows the concentration of power dissipated in chambers for the VR vector, and shows that the VR vector is largely sensitive to the blood dynamics in the superior vena cava.

Figure 5:
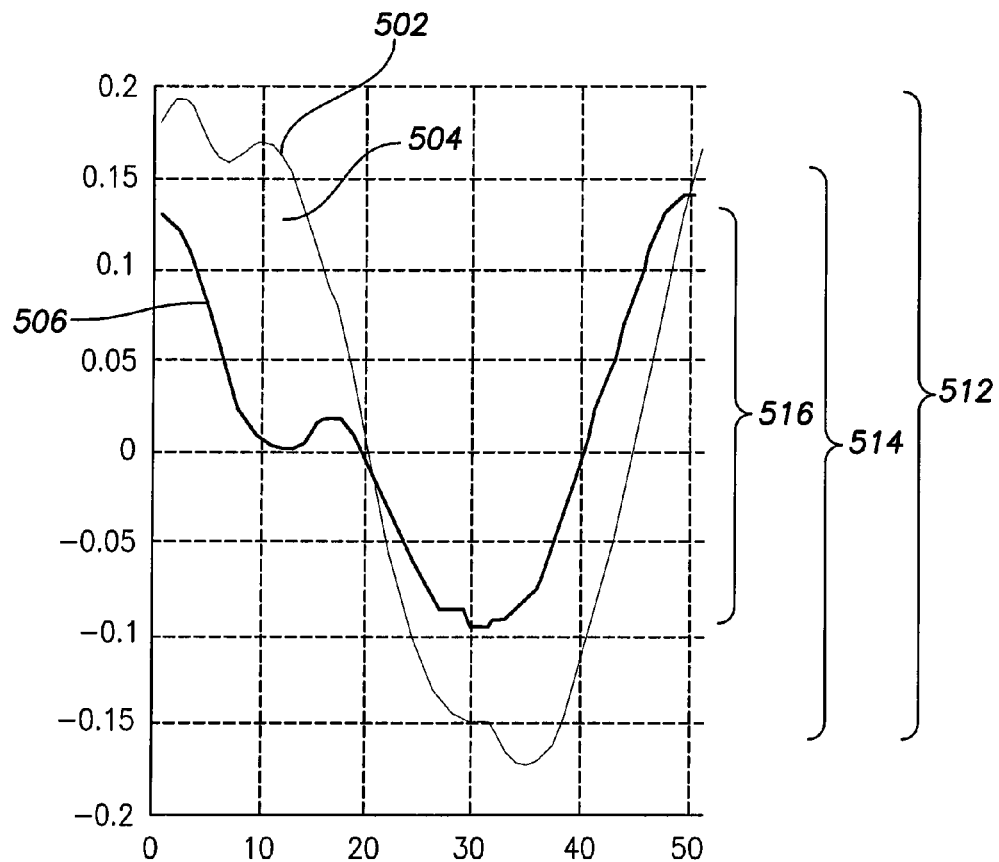
FIG. 5 illustrates DI morphologies plotting examples of DI data sets recorded along a VR vector to show an effect of fluid loading on the impedance recording.

FIG. 5 illustrates DI morphologies 502, 504, and 506 plotting examples of DI data sets recorded along a VR vector to show an effect of fluid loading on the impedance recording. When heart failure (HF) occurs, a subject experiences fluid accumulation also referred to as fluid loading. The fluid accumulation or loading persists over the entire cardiac cycle, including before, during and after influx and discharge of normal venous return blood flow. Given that a larger amount of fluid remains along the VR vector throughout the cardiac cycle, the DC component of the impedance decreases for the duration of the period of time in which fluid loading persists. FIG. 5 illustrates examples of DI morphologies 502, 504 and 506 that may be sensed based on whether the patient is experiencing fluid loading.

In FIG. 5, the horizontal axis represents time and the vertical axis represents impedance centered about a 0 ohm level. The DI morphology 506 corresponds to a high level of fluid loading and higher stroke volume (e.g., 24 ml stroke volume). The DI morphology 504 corresponds to a medium level of fluid loading and medium stroke volume (e.g., 21 ml stroke volume). The DI morphology 502 corresponds to a lower level of fluid loading and higher stroke volume (e.g., 20 ml stroke volume). With more fluid loading indicated by higher SV in DI morphology 506, the peak to peak amplitude decreases with fluid accumulation and redistribution during volume overload.

As illustrated in FIG. 5, when the stroke volume increased (e.g., by 5 ml), the amplitude of the DI data recording decreased. For example, DI morphology 506 has a peak to peak amplitude 516. DI morphology 504 has a peak to peak amplitude 514. DI morphology 502 has a peak to peak amplitude 512.

Then the patient experiences fluid loading, this increases the pre-load experienced by the heart. Preload is the end volumetric pressure that stretches the right or left ventricle of the heart to its greatest geometric dimensions under variable physiologic demand. In other words, preload is the initial stretching of the cardiac myocytes prior to contraction. In the example of FIG. 5, the DI morphology 502 would exhibit the least degree of preload due to fluid accumulation, whereas the DI morphology 506 would exhibit the largest degree of preload due to fluid accumulation.

In the presence of dramatic changes in pre-load, it may be difficult to deduce hemodynamic changes related to stroke volume because preload also modulates the impedance signal. As the degree of preload increases, this causes greater dilation of the SVC/IVC regions. As the SVC/IVC regions undergo greater dilation, this decrease the dynamic peak to peak amplitude of the DI data. Hence, as the SVC/IVC regions undergo greater dilation, DI data becomes less correlated to VR.

In accordance with the methods and systems described herein, the VR vector can be used to select desired (e.g., optimized) hemodynamics provided that pre-load remains within certain limits. When pre-load exceeds such limits, then the DI data begins to exhibit larger variance from the VR. Pre-load can be modulated by volume loading (salt, diuretics) and posture.

Returning to FIG. 1B, at 108, the method analyzes at least one morphologic characteristic from the DI data based on one or more VR-DI correlation metric to obtain a VR indicator associated with the CC. As shown in the examples of FIGS. 2A and 2B, VR-DI correlations metrics may be defined for peak to peak amplitude (dZ) derivative of the negative portion of the DI data (dZ/dt), minimum impedance (MinZ) and the like. The VR-DI correlation metric may optionally represent a correlation between a mean pulmonary arterial pressure (mean PAP) and at least one of i) the P-P amplitude, ii) the MinZ or iii) the dZ/dt. The VR-DI correlation metric may represent at least one of i) a relation between changes in the P-P amplitude and changes in SV, VR and contractile strength, and ii) a relation between changes in the slope of the DI data and changes in direction and degree of cardiac contractility. The analyzing operation includes determining, as the morphologic characteristic, at least one of i) a peak to peak (P-P) amplitude, ii) a MinZ, iii) the dZ/dt or iv) slope, of the DI data as plotted over a temporal time line for at least one CC.

For example, at 108, the method may apply a VR-DI correlation metric by analyzing DI data (such as by plotting the DI data over time as in FIG. 2A) to identify the peak to peak amplitude. The DI morphology 252 may be measured while one set of IMD therapy parameters are set. At 108, the method would identify the maximum peak 274 and the minimum peak 276 from the DI morphology 252. Based on the maximum and minimum peaks 274 and 276, the peak to peak amplitude 262 would be calculated as a VR indicator.

At 109 the VR indicators are stored in memory, along with the present IMD therapy parameter values. The VR indicators and IMD therapy parameter values may be transmitted to an external programmer or network or database for storage.

Next, during a subsequent iteration through the method of FIG. 1B, the IMD therapy parameters would be changed, such as by increasing or decreasing the AV delay by a predetermined step or automatically determined AV change. By way of example, during this subsequent (second) iteration through the method of FIG. 1B, the sensed DI data form DI morphology such as the DI morphology 254. When the DI morphology 254 is sensed, then at 108, the maximum peak 278 and the minimum peak 280 would be identified. The method would then calculate peak to peak amplitude 261 as a VR indicator. The peak to peak amplitude 261 would be stored (at 109) in memory with the present IMD therapy parameter values as a VR indicator.

Alternatively, or in addition, at 108, the method may apply a VR-DI correlation metric by analyzing DI data (such as in FIG. 2B) to identify the dZ/dt. During a first iteration through the method of FIG. 1B, the DI morphology 212 may be measured while one set of IMD therapy parameters are set. At 108, the method would identify the slope throughout the region 216 between maximum and minimum peaks 213 and 215 from the DI morphology 212. At 108, the method would then calculate the maximum negative slope within the region 216 as a VR indicator. The maximum negative slope is then stored (at 109) in memory with the first set of IMD therapy parameter values.

At 110, the method determines whether the options at 102-108 should be repeated for one or multiple cardiac cycles with new IMD therapy parameters. If the process is to be repeated for a new set of IMD therapy parameters, flow moves to 112.

At 112, the method changes or modulates at least one IMD therapy parameter. For example, the AV delay may be adjusted. As another example, the pacing location, pacing pulse amplitude, pacing pulse duration, pacing pulse interval and the like, may be adjusted. The AV delay or other IMD therapy parameters may be adjusted by a predetermined set amount of time, or by a variable amount of time. Optionally, the AV delay or other IMD therapy parameter may be adjusted by an amount determined automatically based on the patients past and/or current physiologic behavior.

The IMD therapy parameters would be changed, such as by increasing or decreasing the AV delay. By way of example, during this subsequent (second) iteration through the method of FIG. 1B, the sensed DI data form DI morphology such as the DI morphology 210. When the DI morphology 254 is sensed, then at 108, the maximum and minimum peaks 217 and 219 would be identified. Then the method would analyze the slope throughout the region 214 between maximum and minimum peaks 217 and 219. At 108, the method would then calculate the maximum negative slope, as a VR indicator, within the region 214. The maximum negative slope is then stored (at 109) in memory, as a VR indicator, with the second set of IMD therapy parameter values.

Optionally, the modulation may adjust an IMD therapy configuration based on the collection of VR indicators and the VR-DI correlation metric such that the IMD operates to encourage a select VR level. To adjust the IMD therapy configuration, the method may determine a select level for the at least one IMD therapy parameter that provides at least one of i) a select peak to peak amplitude, ii) a select minimum amplitude, iii) a select DI change per unit time (dZ/dt) or iv) a select slope, of the DI data when plotted over time.

Next, flow returns to 102 and the above operations are repeated. The operations at 102 to 114 may be repeated a desired number of times to obtain a collection of VR indicators associated with different IMD therapy parameters.

Once the operations at 102-108 are performed a desired number of times, flow jumps to 116. At 116, the method identifies the new IMD therapy configuration that yields desired cardiac function, as indicated by the DI data. To do so, the VR indicators (and optionally DI data) are analyzed to identify one of IMD therapy configurations that yields a desired or select level of VR. For example, the VR indicators, DI data and IMD therapy parameter settings may be stored in a table at 109. At 116, the method may select the VR indicator(s) that satisfy a threshold or fall within a desired range. Once a desired VR indicator(s) is chosen, the method obtains the associated IMD therapy parameter settings that induced in the VR indicators. At 116, the method adjusts the IMD therapy configuration to match the chosen IMD therapy parameter settings such that the IMD operates to encourage a select VR level.

As explained above, the DI data may be collected and analyzed in connection with a select activity state and a select posture position of a patient. For example, a threshold decision block may be added (such as at 105). The method may determine whether the patient is in a select activity state and/or a select posture position. For example, it may be desirable to only perform the operations of FIG. 1B when the patient is standing or sitting, and not while laying down. In this example, when the patient lays down, flow through the process of FIG. 1B would stop and wait until the patient stands up or sits up. Similarly, when the patient is in a certain activity state (e.g., at rest, walking, light exertion), the process of FIG. 1B may be implemented. However, when the patient is undergoing strenuous exercise, it may be desirable to not perform the process of FIG. 1B. For example, in certain patients undergoing strenuous exercise, the DI data may not correlate as closely to actual venous return volume. Hence, in such patients, the IMD parameters are not modified based on DI data during strenuous exercise.

Alternatively, in certain instances, the IMD parameters may be set while the patient is in a known posture and/or activity state. When the patient's posture and/or activity level varies from the posture/activity level, that was utilized when setting the IMD parameters, then it may be desirable to perform the process of FIG. 1B to establish new IMD parameter settings in connection with a current posture/activity level.

The posture and/or activity level may affect an amount of preload experienced by the patient. When preload varies, it may not be desirable to modify the IMD parameters based on DI data. However, when preload is the same, one IMD parameter that may be varied is AV delay. The AV delay may be modulated to determine the best AV delay for the patient. For example, the process may determine the pacing configuration that provides the VR-DI correlation with the highest peak to peak amplitude in the DI data (which indicates a high stroke volume and venous return), while choosing the configuration that provides the lowest dZ/dt (which indicates low contractility and hence metabolic demand). Depending on a patient's need and disease state, a configuration may be chosen with a combination of high DI P-to-P amplitude and low dZ/dt can be chosen (to prevent stressing the heart). Alternatively, a configuration may be chosen with a combination of high DI P-to-P amplitude and high dZ/dt such as to yield high cardiac performance for the duration of peak activity.

By way of example, for sick patients, it is may be desirable to implement option i) above for the most part of the day, namely a combination of high DI P-to-P amplitude and low dZ/dt can be chosen. Then for a short duration of activity, option ii) can be used, namely a configuration may be chosen with a combination of high DI P-to-P amplitude and high dZ/dt such as to yield high cardiac performance for the duration of peak activity.

As noted herein, during respiratory inspiration, the venous return increases. In certain embodiments, the relation between respiratory cycle and VR may be actively managed. For example, the method may modulate the AV delay in synchronization with the venous return to allow for a desired level of SV on a continual basis.

Also, venous return may be significantly affected by body position. In such instances, it may be desirable to track the venous return on a continual basis even while the patient is in a prone position. For example, tracking VR continuously helps identify compromised venous return while the patient is lying on his/her side or in other body positions (e.g., right side lying or different body positions). When VR volume drops below a lower threshold, the patient can either be prompted to change the body position (via a tactile warning), or the pacing configuration and or AV/VV delays can be changed to provide the best hemodynamic state for the patient in that particular body position, which otherwise would result in an compromised hemodynamic state.

Figure 6:
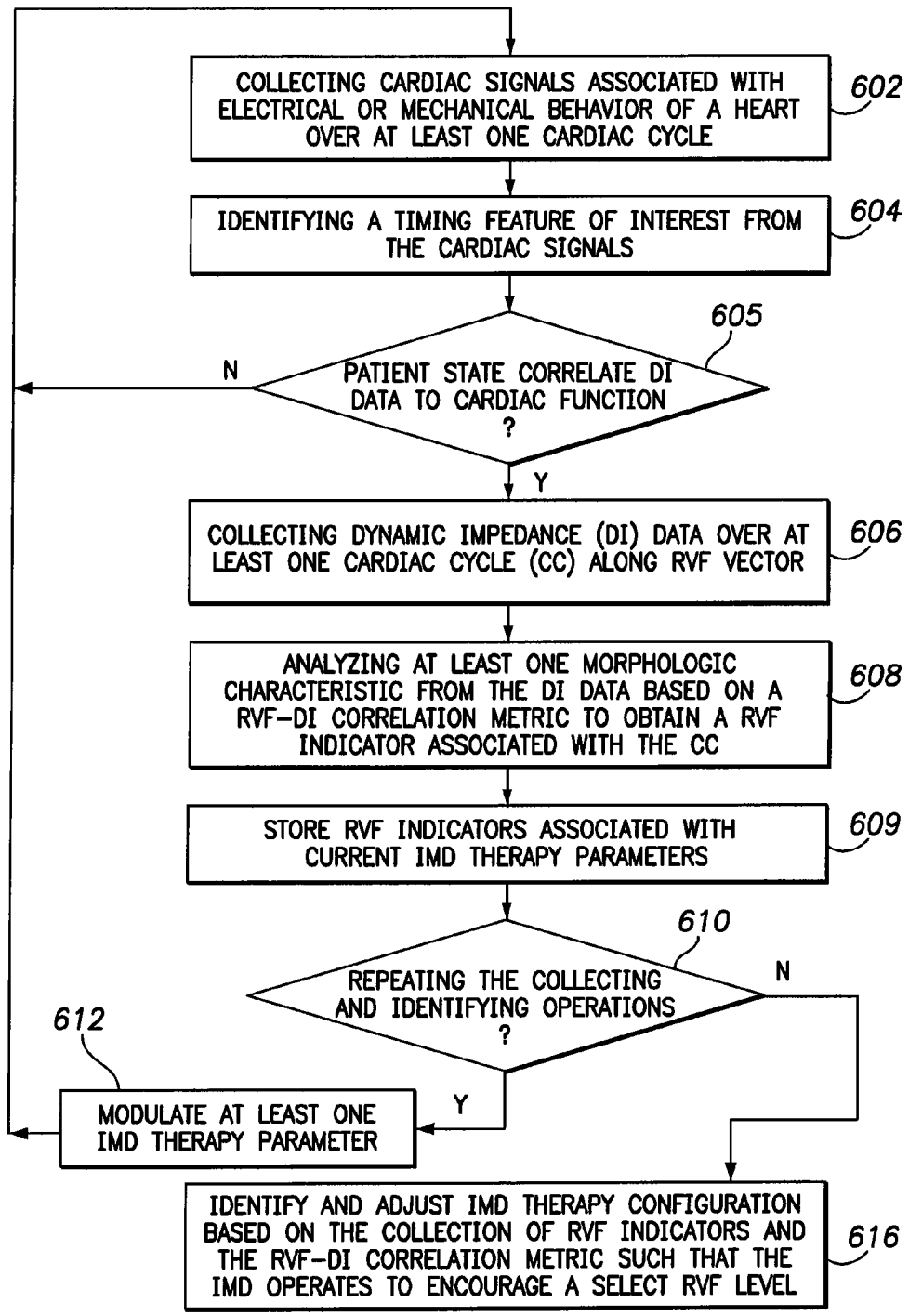
FIG. 6 illustrates a right ventricular cardiac function characterization method to be carried out in accordance with an embodiment by one or more of an IMD, external programmer and system described herein.

FIG. 6 illustrates a right ventricular cardiac function characterization method 600 to be carried out in accordance with an embodiment by one or more of an IMD, external programmer and system described herein. The method of FIG. 6 begins with IMD therapy parameters set to predetermined values and/or set manually or automatically by the IMD, based on conventional programming techniques. The IMD therapy parameters may include one or more of AV delay, VV delay, pacing electrode combination, stimulus pulse width, strength, interval and the like.

Beginning at 602, the method collects cardiac signals associated with electrical and/or mechanical behavior of a heart over at least one cardiac cycle while an IMD operates based on current IMD therapy parameter values.

At 604, the method identifies a timing FOI from the cardiac signals. For example, the timing feature of interest may be the peak of the R-wave, the start or center of the P-wave, the ST segment, and the like. The timing feature may be intrinsic or paced. When the cardiac signal is indicative of mechanical behavior, the timing feature of interest may represent the amount of movement, the orientation of the patient and the like.

At 605, the method utilizes the timing FOI to determine whether the patient is in a state in which dynamic impedance data, if acquired, would substantially correlate to the cardiac function of interest. For example, the method may utilize the cardiac signals to identify an arrhythmia, determine the heart rate, and determine a starting point for a cardiac cycle, an exertion level, patient orientation and the like. The patient state may be used to determine whether to perform subsequent DI data collection and analysis. For example, when the patient state indicates that the patient is experiencing an excessively high heart rate, flow may return to 602 and/or the method may determine to cease operation for a period of time or a predetermined number of cardiac cycles. As explained herein, when the patient is undergoing heavy excursion, the DI data may not substantially track RVF as closely as desired. The degree to which DI data is expected to track or correlate to RVF may be characterized in terms of variance, deviation and the like. At 605, the method may use predetermined, select or automatically updated, thresholds for one or more timing features of interest. When the measured cardiac signal exceeds (or falls below) a threshold, the method may determine at 605 that too much variance exists between DI data and the RVF for present patient state. Alternatively, at 605 when the patient state indicates that the DI data should correlate to RVF, then flow moves to 606.

At 606, the method collects dynamic impedance data for a collection window over at least one cardiac cycle along at least one vector of interest, such as a right ventricular function vector. The RVF vector may be aligned such that changes in the DI data substantially correlate with changes in RVF, such as systolic function, diastolic function, and a surrogate for mitral valve closure timing and mitral valve opening timing. For example, the RVF vector may extend through the RV, and through a portion of one or more other chambers, tissue and the like. Current flux density at the surface of the RV electrode (e.g., RV coil, RV ring or RV tip) is relatively high as compared to the current flux density remote from the RV electrode (e.g., at other chambers of the heart or outside of the heart). Due to the substantially larger current flux density immediately adjacent the RV electrode, the DI data is primarily affected by changes in the impedance in the area (e.g., the blood) immediately surrounding the RV electrode, while changes in the impedance in areas more remote from the RV electrode have less relative impact on changes in the dynamic impedance.

For example, the collecting operation may collect the DI data along a RVF vector that is defined by an IMD case electrode and at least one of an RV coil electrode, an RV tip electrode and an RV ring electrode. The select combination of electrodes that defines the RVF vector is used to collect the DI data. When the RV coil to case electrode combination is used, the DI signal will exhibit upward inflection during ventricular ejection and downward deflection during ventricular filling. The slope of the deflection will change in correlation with changes in contractility. The peak to peak amplitude will change with stroke volume and the force of contractility.

Optionally, different electrode combinations may be used to collect subsets of the DI data, where each subset of DI data may be analyzed for a common, or for different, morphologic characteristics, where the subsets of DI data collectively track the RVF.

Figure 7A:
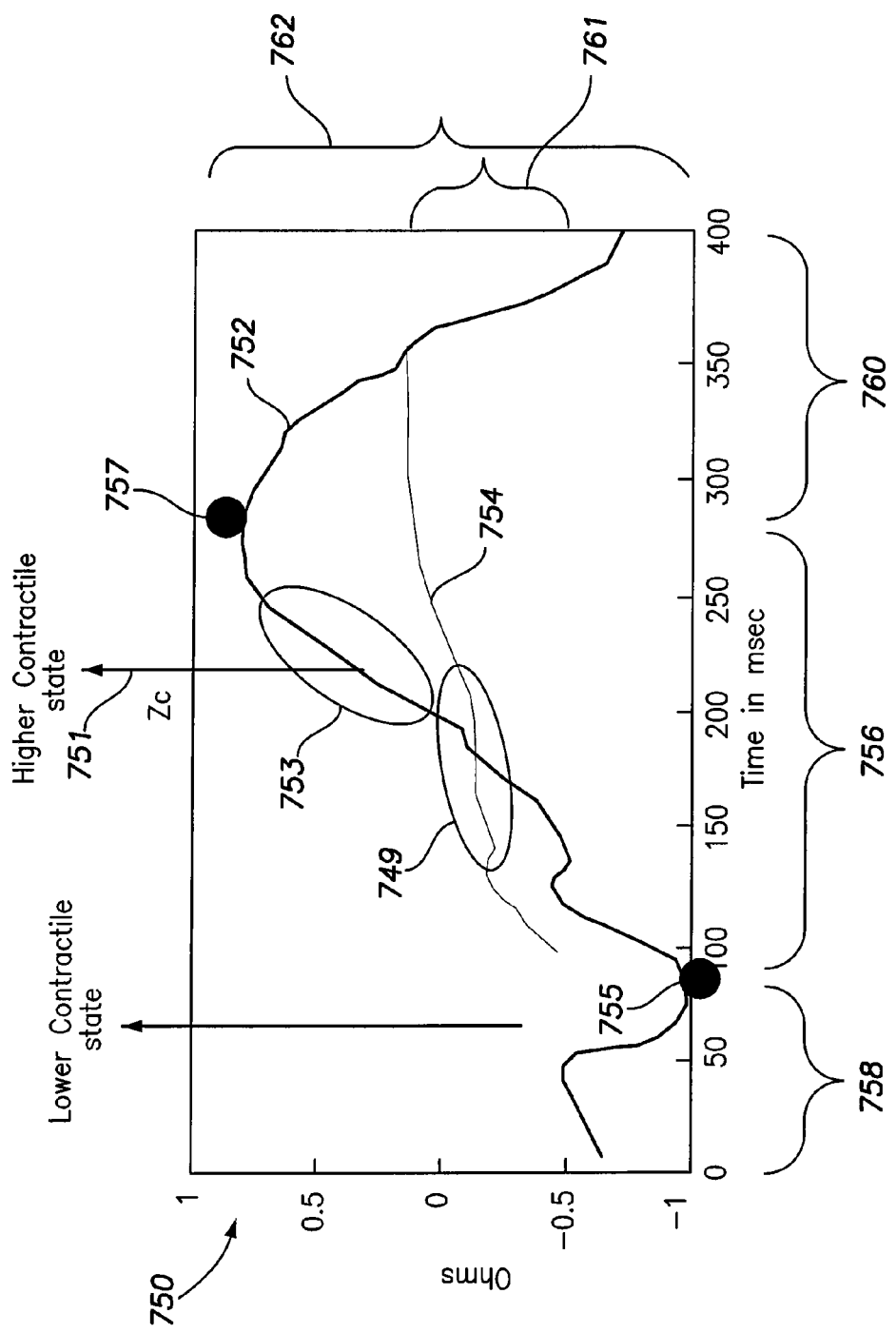
FIG. 7A illustrates a graph plotting examples of DI morphologies for patients having different stroke volumes utilizing the RV coil to case electrode combination in accordance with an embodiment.

FIG. 7A illustrates a graph 750 plotting examples of DI morphologies 752 and 754 for patients having different stroke volumes utilizing the RV coil to case electrode combination. The graph 750 plots time along the horizontal axis and dynamic impedance along the vertical axis. The y-axis corresponds to impedance in Ohms. The y-axis includes a zero level and extends +1/−1 Ohm. It should be recognized that FIG. 7A is an example of the dynamic component of the measured impedance. As in the embodiment of FIG. 1B, the impedance measurement will also have a DC component that is subtracted from graph 750. The DI data has been normalized after subtracting the DC bias component.

The x-axis extends over a 400 ms period representing one cardiac cycle. The 0 ms point represents the V pace marker at which a paced event occurred and is used as the cardiac feature of interest to form the start of a DI data collection window. The cardiac cycle includes a ventricular systole period 756 and a ventricular diastole period (collectively represented by 758 and 760).

The DI vector morphologies 752 and 754 are characteristic of RVF when applying one or more RVF-DI correlation metrics to the DI data collected along one or more RVF vectors. The plots of FIG. 7A illustrate DI morphologies 752 and 754, both associated with a paced heart rate of 150 bpm. The DI morphology 752 includes DI data collected while the IMD therapy parameters were set with an AV delay of 80 ms while the patient received dobutamine. The RVF-DI correlation 754 includes DI data collected while the IMD therapy parameters were set with an AV delay of 80 ms and while the patient did not receive dobutamine.

The upward deflections (such as between 755 and 757 in the DI morphology 752) correspond to ventricular emptying, whereas the downward deflections (such as before 755 or after 757 in the DI morphology 752) correspond to ventricular filling. The durations, and shapes of the DI data during, the ventricular emptying and filling phases of the cardiac cycle are indicative of a degree or quality of the right ventricular function.

The DI morphologies 752 and 754 exhibit various characteristics of interest that are indicative of cardiac function of interest when RVF-DI correlation metrics are applied. One RVF-DI correlation metric or feature of interest from the RVF vector, to be used for determining ventricular functionality, is peak to peak amplitude. The DI morphologies 752 and 754 have peak to peak amplitudes 762 and 761, respectively. Changes in the peak to peak amplitude 762 of the impedance signal directly correlates to stroke volume and contractility strength. The peak to peak amplitude increase with increase SV and increased contractile strength. The DI morphology 752 exhibits larger peak to peak amplitude 762 in the DI data of the associated RVF, as compared to the peak to peak amplitude 761 for an associated RVF. In general, it is desirable for the DI data to exhibit larger peak to peak amplitude as this is an indication of larger RVF. When the peak to peak amplitude increases this is indicative of an increase in RVF.

Another RVF-DI correlation metric is the derivative or slope of the DI morphology during the positive or up stroke of the DI data, referred to a dZ/dt. The derivative (or slope) of the up-stroke of the impedance signal forming the DI morphologies 752 and 754 are indicative of, and directly correlate to, the cardiac contractility strength. When the derivative or slope increases, this is indicative of an increase in contractility strength. When the derivative or slope decreases, this is an indication of a decrease in cardiac contractility strength. Similarly, when the derivative/slope of the RVF-DI morphologies 752 or 754 increases, this is an indication of an increase in cardiac contractility.

The derivative of the upstroke portion of the DI morphology correlates well to cardiac contractility. The derivative of the upstroke portion increases with increased contractility and decreases with decreased contractility. For example, in the DI morphology 752, an upstroke portion 753 has a largest positive slope or derivative at point 751. The DI morphology 754 includes an upstroke portion 749 that has a smaller positive slope or derivative (no specific point is designated). Hence, the DI morphology 752 indicates that the associated RVF exhibits a high contractile state, while the DI morphology 754 indicates that the associated RVF exhibits a low contractile state.

Another RVF-DI correlation metric is the duration of the emptying and filling times for the ventricles which occur in conjunction with valve opening and closure. Although the DI data does not directly detect the opening and closure of valve flaps, the DI data represents a mechanical sensory indicatory that indicates blood flow changes that occur gated with valve timings. For example, points of transition between positive and negative slope of the DI morphology are indicative of valves opening and closing. The points 757 and 755 can be utilized to as surrogates for systolic timing. For example, the point 755 represents the point at which the DI data changes from a negative slope to a positive slope, thereby indicating a beginning of the systole phase. The point 757 represents the point at which the DI data changes from a positive slope to a negative slope, thereby indicating an ending of the systole phase. It may be desirable to change the length of the ventricular emptying and/or filling times.

In certain patients, other indicators of cardiac function may offset or out-weight the benefit of setting the IMD parameters to facilitate the largest potential venous return volume. For example, a patient's physiologic state may exhibit an unduly high pulmonary arterial pressure at elevated RVF volumes. When a patient exhibits unduly high PAP, it may be beneficial to target a lower RVF volume (and associated peak to peak amplitude in DI data) that is also associated with a desired or select PAP level.

Figure 7B:
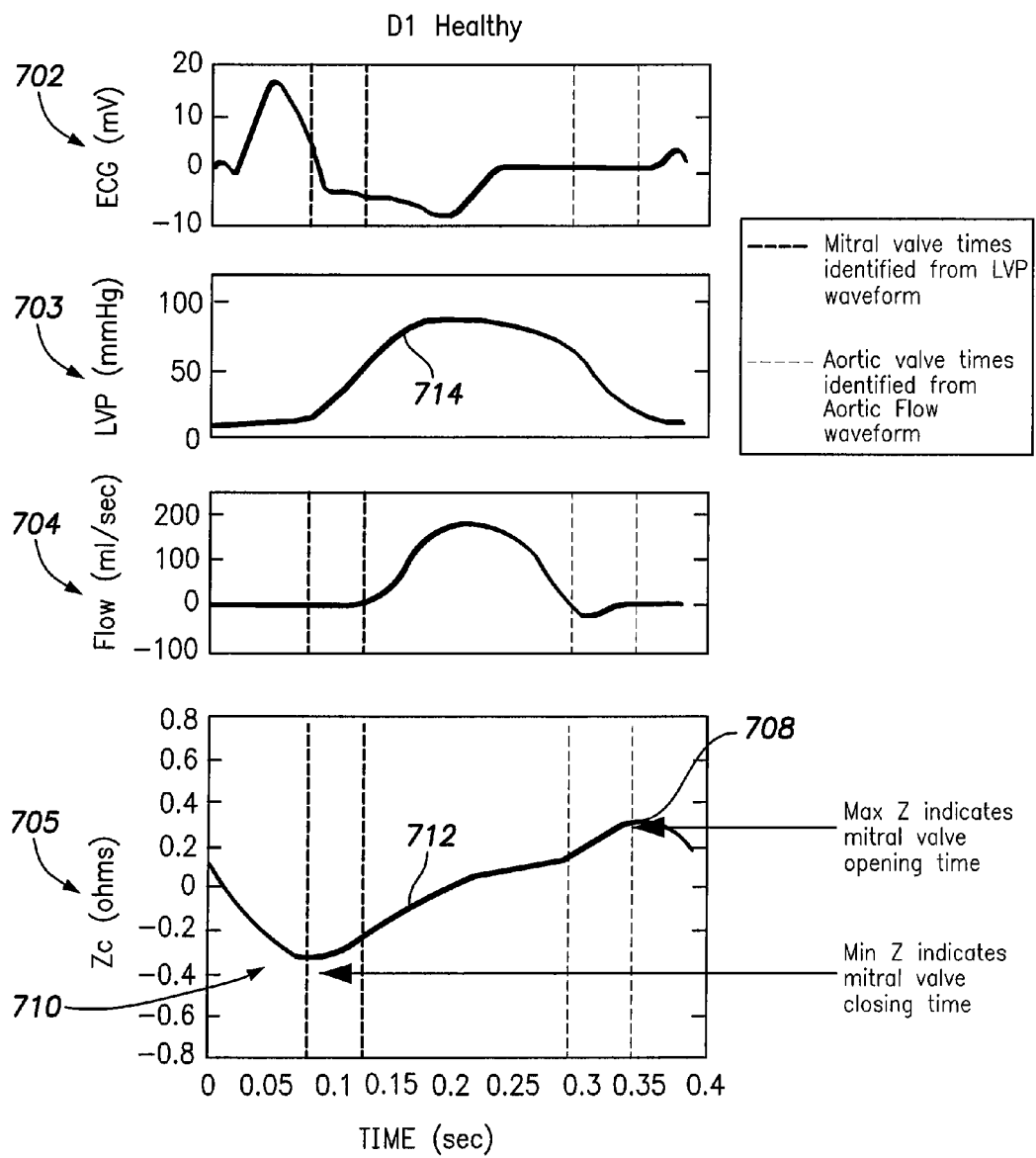
FIG. 7B illustrates a series of graphs associated with one exemplary cardiac cycle.

FIG. 7B illustrates a series of graphs 702-705 associated with one exemplary cardiac cycle. The graphs 702-705 include time along the horizontal axis. The graph 702 plots an ECG signal along the vertical axis. The graph 703 plots left ventricular pressure (LVP) along the vertical axis associated with a single cardiac cycle. The graph 704 plots cardiac flow along the vertical axis, and the graph 705 plots DI data for dynamic impedance measured along at least one RVF vector for the associated cardiac cycle. In the plot 705 of DI data, maximum and minimum points 708 and 710 are designated. The points 708 and 710 represent the points at which a slope of the RVF morphology 712 changes from positive to negative (for point 708) and from negative to positive (for point 710). The point 710 represents a minimum impedance value which indicates the point in time at which the mitral valve closes (MVC time). The point 708 represents a maximum impedance value (MaxZ) which indicates the point in time at which the mitral valve opens (MVO time). By monitoring the RVF morphology and identifying the maximum and minimum impedances, these measurements can be used as surrogates for the MVC and MVO points in time.

Figure 8:
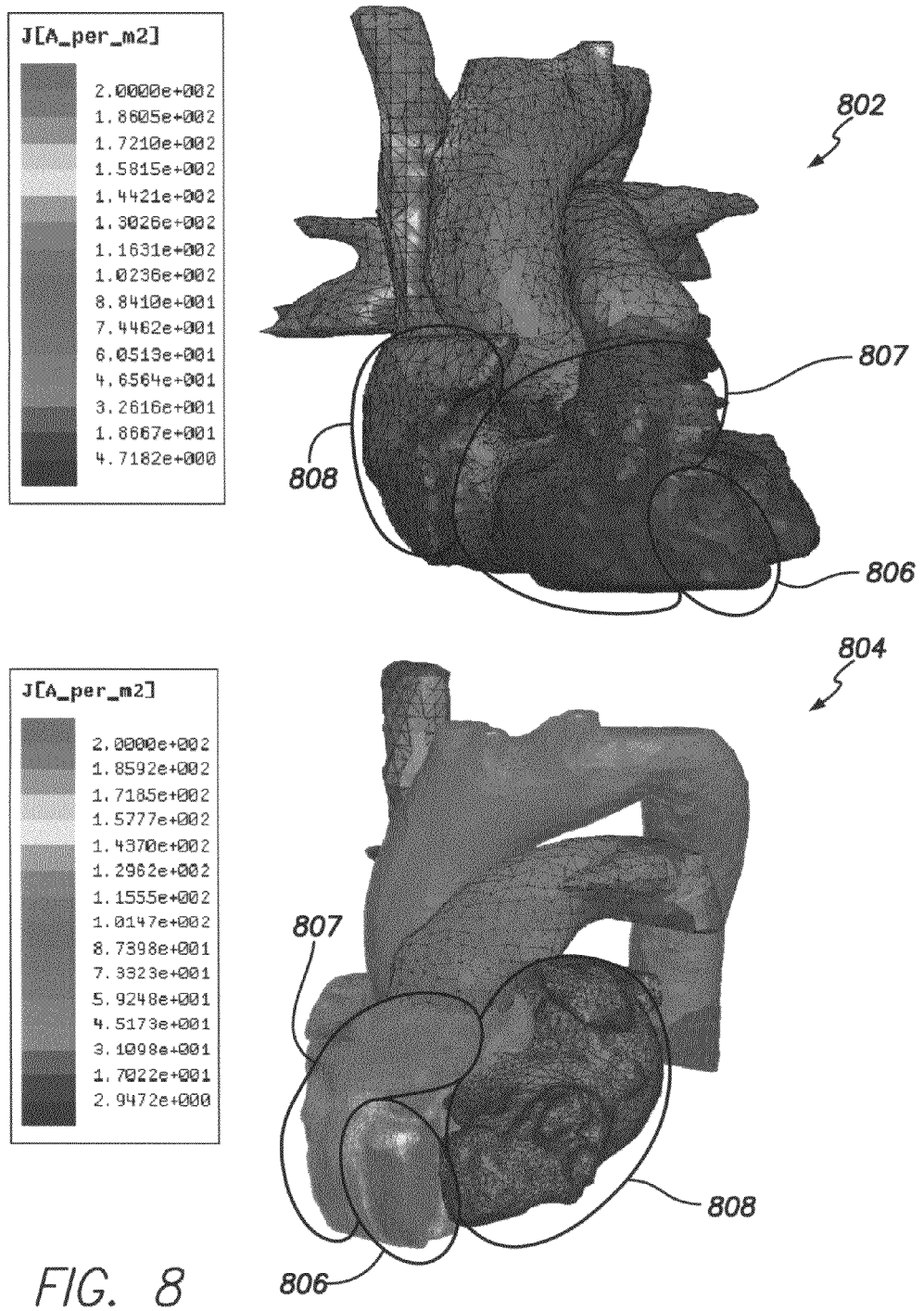
FIG. 8 illustrates computer models that were generated based on lead field theory.

FIG. 8 illustrates computer models 802 and 804 that were generated based on lead field theory. The models 802 and 804 illustrate different views of the heart with certain regions 806-808 circled. The circled regions 806-808 correspond to regions of the heart that exhibit different current flux densities at select points during the cardiac cycle. The current flux density in the region 806 is substantially higher as compared to the current flux density in the regions 807 and 808 during the peak systolic phase. The regions 806 corresponds to the apex of the RV, while the region 807 corresponds to other portions of the RV and RA. The region 808 corresponds to the LV. Because the current flux density is highest (relatively) in the region 806 proximate the RV apex at peak systolic phase, changes in the dynamic impedance proximate to the RV apex will substantially affect the DI data measured. Because the current flux density is lowest (relatively) in the region 808 proximate the LV apex at peak systolic phase, changes in the dynamic impedance proximate to the LV will not substantially affect the DI data measured at this time. Hence, the models 802 and 804 show that the impedance RVF vector is most affected by the blood in the right ventricle. The models 802 and 804 show concentration of power dissipated during peak systolic phase of the cardiac cycle in the corresponding chambers for the RVF vector. As shown in FIG. 8, the RVF vector is very sensitive to the blood dynamics in the right ventricular apex.

Returning to FIG. 6, at 608, the method analyzes at least one or more morphologic characteristics from the DI data based on one or more RVF-DI correlation metric to obtain a RVF indicator(s) associated with the CC. As shown in the examples of FIGS. 7A and 7B, RVF-DI correlations metrics may be defined for peak to peak amplitude, the derivative of the positive portion of the DI data (dZ/dt) during the systolic phase, the minimum impedance (MinZ), the maximum impedance and the like. The RVF-DI correlation metric may represent at least one of i) a relation between changes in the P-P amplitude and changes in RVF and/or contractile strength, and ii) a relation between changes in the slope of the DI data and changes in direction and degree of cardiac contractility.

For example, at 608, the method may apply a RVF-DI correlation metric by analyzing DI data (such as in FIG. 7A) to identify the peak to peak amplitude. The DI morphology 752 may be measured while one set of IMD therapy parameters are set. At 608, the method would identify the maximum peak 774 and the minimum peak 776 from the DI morphology 752. Based on the maximum and minimum peaks 774 and 776, the peak to peak amplitude 762 would be calculated as a RVF indicator.

At 610 the RVF indicator is stored in memory, along with the present IMD therapy parameter values.

At 610, the method determines whether the options at 602-608 should be repeated for one or multiple cardiac cycles with new IMD therapy parameters. If the process is to be repeated for a new set of IMD therapy parameters, flow moves to 612.

At 612, the method changes or modulates at least one IMD therapy parameter. For example, the AV delay may be adjusted. As another example, the pacing location, pacing pulse amplitude, pacing pulse duration, pacing pulse interval and the like, may be adjusted. The AV delay or other IMD therapy parameters may be adjusted by a predetermined set amount of time, or by a variable amount of time. Optionally, the AV delay or other IMD therapy parameter may be adjusted by an amount determined automatically based on the patients past and/or current physiologic behavior.

The IMD therapy parameters would be changed, such as by increasing or decreasing the AV delay by a predetermined step or automatically determined AV change. By way of example, during this subsequent (second) iteration through the method of FIG. 1B, the sensed DI data form DI morphology such as the DI morphology 754. When the DI morphology 754 is sensed, then at 608, the maximum peak 778 and the minimum peak 780 would be identified. The method would then calculate peak to peak amplitude 761 as a RVF indicator. The peak to peak amplitude 761 would be stored (at 609) in memory with the present IMD therapy parameter values as a RVF indicator.

Alternatively, or in addition, at 608, the method may apply a RVF-DI correlation metric by analyzing DI data (such as in FIG. 7B) to identify the dZ/dt. During a first iteration through the method of FIG. 1B, the DI morphology 712 may be measured while one set of IMD therapy parameters are set. At 608, the method would identify the slope throughout the region 716 between maximum and minimum peaks 713 and 715 from the DI morphology 712. At 608, the method would then calculate the maximum negative slope within the region 716 as a RVF indicator. The maximum negative slope is then stored (at 609) in memory with the first set of IMD therapy parameter values.

Next, during a subsequent iteration through the method of FIG. 1B, the IMD therapy parameters would be changed, such as by increasing or decreasing the AV delay. By way of example, during this subsequent (second) iteration through the method of FIG. 1B, the sensed DI data form DI morphology such as the DI morphology 760. When the DI morphology 754 is sensed, then at 608, the maximum and minimum peaks 717 and 719 would be identified. Then the method would analyze the slope throughout the region 714 between maximum and minimum peaks 717 and 719. At 608, the method would then calculate the maximum negative slope, as a RVF indicator, within the region 714. The maximum negative slope is then stored (at 609) in memory, as a RVF indicator, with the second set of IMD therapy parameter values.

Optionally, the modulation may include adjusting an IMD therapy configuration based on the collection of RVF indicators and the RVF-DI correlation metric such that the IMD operates to encourage a select RVF level. To adjust the IMD therapy configuration, the method may determine a select level for the at least one IMD therapy parameter that provides at least one of i) a select peak to peak amplitude, ii) a select minimum amplitude, iii) a select DI change per unit time or iv) a select slope, of the DI data when plotted over time.

Next, flow returns to 602 and the above operations are repeated. The operations at 602 to 612 may be repeated a desired number of times to obtain a collection of RVF indicators associated with different IMD therapy parameters.

Once the operations at 602-609 are performed a desired number of times, flow jumps to 616.

At 616, the method identifies the new IMD therapy configuration that yields desired cardiac function, as indicated by the DI data. To do so, the RVF indicators and DI data are analyzed to identify one of IMD therapy configurations that yield a desired or select level of RVF. For example, the RVF indicators, DI data and IMD therapy parameter settings may be stored in a table at 614. At 616, the method may select the RVF indicator(s) that satisfy a threshold or fall within a desired range. Once a desired RVF indicator(s) is chosen, the method obtains the associated IMD therapy parameter settings that induced in the RVF indicators. At 616, the method adjusts the IMD therapy configuration to match the chosen IMD therapy parameter settings such that the IMD operates to encourage a select RVF level.

As explained above, derivative of the impedance (systolic phase) changes with contractility. In some subjects, at 616, the clinician might want to use a pacing/lead configuration that increases the ventricular emptying and contractility. However, in sicker individuals, it may be preferred at 616 to use a configuration that does not stress the heart and has lower contractile state.

Optionally, in certain subjects, it may be desirable to change the IMD therapy parameters to achieve a desired level for the diastolic function and increase the diastolic time while decreasing the contractility. An affect of set values for the IMD therapy parameters can be identified through the DI morphology of the dynamic impedance data. As an example, an DI morphology can be stored as a profile and the slope and timing from the DI morphology can be used for optimization to tailor the IMD therapy parameters for a given subject.

Figure 9:
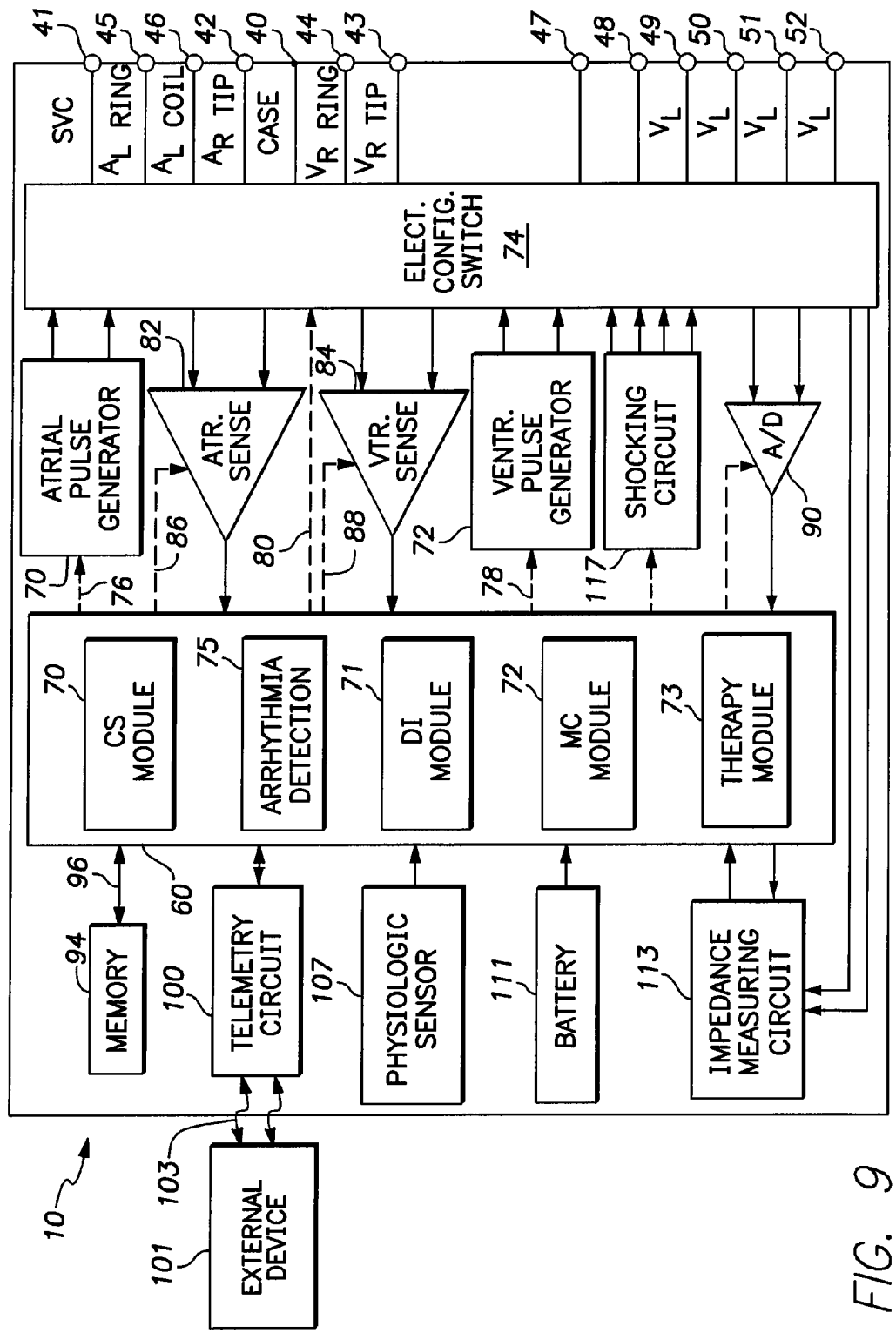
FIG. 9 illustrates a block diagram of an IMD configured to implement the methods described herein to characterize cardiac function in accordance with an embodiment.

FIG. 9 illustrates a block diagram of the IMD 10, which is capable of performing the methods described herein and of treating one or both of fast and slow arrhythmias with stimulation therapy, including cardioversion, defibrillation, and pacing stimulation. While a particular multi-chamber device is shown, this is for illustration purposes only. It is understood that the appropriate circuitry could be duplicated, eliminated or disabled in any desired combination to provide a device capable of simply monitoring impedance and/or cardiac signals, and/or treating the appropriate chamber(s) with cardioversion, defibrillation and pacing stimulation.

The housing 40 for the stimulation IMD 10 is often referred to as the "can", "case" or "case electrode" and may be programmably selected to act as the return electrode for some or all sensing modes. The housing 40 may further be used as a return electrode alone or in combination with one or more of the electrodes of FIG. 1 for shocking purposes. The housing 40 further includes a connector (not shown) having a plurality of terminals 41-52. To achieve sensing, pacing and shocking in desired chambers of the heart, the terminals 41-52 are selectively connected to corresponding combinations of electrodes 22-38.

The IMD 10 includes a programmable microcontroller 60 that controls the various modes of sensing and stimulation therapy. The microcontroller 60 includes a microprocessor, or equivalent control circuitry, designed specifically for controlling sensing impedance derivation and the delivery of stimulation therapy and may further include RAM or ROM memory, logic and timing circuitry, state machine circuitry, and I/O circuitry. The microcontroller 60 includes the ability to process or monitor input signals (data) as controlled by a program code stored in memory. The details of the design and operation of the microcontroller 60 are not critical to the present invention. Rather, any suitable microcontroller 60 may be used.

The microcontroller 60 may search for a pacing threshold following paced events. The microcontroller 60 may do so by performing an auto capture process to determine whether a paced event successfully captured the surrounding tissue. The microcontroller 60 includes an arrhythmia detection module 75 that analyzes sensed signals and determines when an arrhythmia (e.g., fibrillation) is occurring. The detection module 75 receives signals sensed by electrodes located at sensing sites. The detection module 75 detects arrhythmias, such as ventricular tachycardia (VT), bradycardia and ventricular fibrillation (VF). The microcontroller 60 may include a morphology detection module (not shown) that analyzes the morphology of the cardiac signal. Among other things, the module may detect R wave peaks and/or detect T wave features of interest, such as onset, peak, etc.

The microcontroller 60 includes inputs that are configured to collect cardiac signals associated with electrical or mechanical behavior of a heart over at least one cardiac cycle. The cardiac signals may IEGM signals from the atrial or ventricular sensing circuits 82 and 84 that are representative of electrical behavior of the heart. Optionally, the cardiac signals may be the output of the A/D circuit 90 that are representative of electrical behavior of the heart. The cardiac signals may be the output of the physiologic sensor 108 that are representative of mechanical behavior. As one example, the inputs are configured to collect the DI data utilizing an IMD case electrode and at least one of an SVC electrode, an IVC electrode and an RA electrode to define the VR vector.

The microcontroller 60 includes a CS module 70, a DI module 71, an MC module 72, a therapy module 73 and an arrhythmia detection module 75 (among other things). The cardiac signal (CS) module 70 is configured to identify a timing feature of interest (FOI) from the cardiac signals.

The DI module 71 is configured to collect dynamic impedance (DI) data over at least one cardiac cycle, designated by the timing FOI, along at least one of i) a venous return vector or ii) a right ventricular function vector.

The morphology characteristic (MC) module 72 is configured to analyze at least one morphologic characteristic from the DI data based on at least one of i) a VR-DI correlation metric to obtain a VR indicator associated with the CC or ii) a RVF-DI correlation metric to obtain a RVF indicator associated with CC. The MC module 72 is further configured to determine a select level for the at least one therapy parameter that provides at least one of i) a select peak to peak amplitude, ii) a select minimum amplitude, iii) a select DI change per unit time, iv) a select slope, v) a select ventricular filling time, or vi) a select ventricular emptying time, of the DI data when plotted over time. The MC module 72 is configured to determine, as the morphologic characteristic, at least one of i) a peak to peak amplitude, ii) a minimum amplitude, iii) a minimum DI change per unit time, iv) slope, v) a select ventricular filling time, or vi) a select ventricular emptying time, of the DI data over the CC. The MC module 72 collects and analyzes the DI data in connection with a select activity state and a select posture position of a patient.

The therapy module 73 is configured to modulate, over multiple cardiac cycles, at least one therapy parameter while the IMD 10 obtains a collection of at least one of VR indicators or RVF indicators associated with different therapy parameters. The therapy module 73 is configured to adjust an therapy configuration based on at least one of i) the collection of VR indicators and the VR-DI correlation metric such that the system operates to encourage a select VR level or ii) the collection of RVF indicators and the RVF-DI correlation metric such that the system operates to encourage a select RVF level.

The memory 94 stores correlation metrics associated with the cardiac functions of interest, such as VR-DI and RVF-DI correlation metrics. The VR-DI correlation metric represents a correlation between a mean pulmonary arterial pressure (mean PAP) and at least one of i) the P-P amplitude, ii) the minimum amplitude or iii) the dZ/dt. The VR-DI correlation metric represents at least one of i) a relation between changes in the P-P amplitude and changes in stroke volume and contractile strength, and ii) a relation between changes in the slope of the DI data and changes in direction and degree of cardiac contractility.

The memory 94 also stores the VR indicators, RVF indicators and associated IMD therapy parameter values for each iteration through the methods of FIGS. 1B and 6. Once the IMD 10, system or method determines a new set of IMD therapy parameter values to be used to encourage a select VR or RVF level.

An atrial pulse generator 70 and a ventricular pulse generator 72 generate pacing and ATP stimulation pulses for delivery by desired electrodes. The electrode configuration switch 74 (also referred to as switch bank 74) controls which terminals 41-52 receive shocks or pacing pulses. The atrial and ventricular pulse generators, 70 and 72, may include dedicated, independent pulse generators, multiplexed pulse generators, shared pulse generators or a single common pulse generator. The pulse generators 70 and 72 are controlled by the microcontroller 60 via appropriate control signals 76 and 78, respectively, to trigger or inhibit stimulation pulses. The microcontroller 60 further includes timing control circuitry 79 which is used to control the timing of such stimulation pulses (e.g., pacing rate, atrio-ventricular (AV) delay, atrial interconduction (A-A) delay, or ventricular interconduction (V-V) delay, etc.) as well as to keep track of the timing of refractory periods, PVARP intervals, noise detection windows, evoked response windows, alert intervals, marker channel timing, etc.

An electrode configuration switch 74 connects the sensing electronics to the desired terminals 41-52 of corresponding sensing electrodes 22-38. For example, terminals 49-52 may be coupled to LV electrodes 23-26. The switch 74 may connect terminals 41-52 to one or more ventricular sensing circuits 84, which provide cardiac signals, representative of cardiac activity, to the microcontroller. The circuit 84 may amplify, filter, digitize and/or otherwise process the sensed cardiac signals from the LV electrodes 23-26. The circuit 84 may provide separate, combined or difference signals to the microcontroller 60 representative of the sensed signals from the LV electrodes 23-26. The circuit 84 may also receive sensed signals from RV electrodes 32 and 34 through terminals 43 and 44. The atrial sensing circuit 82 is connected through the switch 74 terminals 42 and 45-46 to desired RA and/or LA electrodes 22 and 27-28 to sense RA and/or LA cardiac activity. The switch 74 also connects various combinations of the electrodes 22-38 to an impedance measurement circuit 113.

An impedance measuring circuit 112 includes inputs to collect multiple measured impedances between corresponding multiple combinations of electrodes 22-38. For example, the impedance measuring circuit 112 may collect a measured impedance for each or a subset of the active sensing vectors 151-155. Optionally, the impedance measuring circuit 112 may also monitor lead impedance during the acute and chronic phases for proper lead positioning or dislodgement; detects operable electrodes and automatically switches to an operable pair if dislodgement occurs; measures respiration or minute ventilation; measures thoracic impedance for determining shock thresholds; detects when the device has been implanted; measures stroke volume; and detects the opening of heart valves, etc.

The switch bank 74 includes a plurality of switches for connecting the desired electrodes to the appropriate I/O circuits, thereby providing complete electrode programmability. The switch 74, in response to a control signal 80 from the microcontroller 60, determines the polarity of the stimulation pulses (e.g., unipolar, bipolar, co-bipolar, etc.) by selectively closing the appropriate combination of switches (not specifically shown). Atrial sensing circuits 82 and ventricular sensing circuits 84 may also be selectively coupled to the right atrial lead 20, LV lead 21, and the RV lead 30, through the switch 74 for detecting the presence of cardiac activity in each of the four chambers of the heart. The switch 74 determines the "sensing polarity" of the cardiac signal by selectively closing the appropriate switches.

The outputs of the atrial and ventricular sensing circuits 82 and 84 are connected to the microcontroller 60 which, in turn, is able to trigger or inhibit the atrial and ventricular pulse generators 70 and 72, respectively. The sensing circuits 82 and 84, in turn, receive control signals over signal lines 86 and 88 from the microcontroller 60 for purposes of controlling the gain, threshold, the polarization charge removal circuitry (not shown), and the timing of any blocking circuitry (not shown) coupled to the inputs of the sensing circuits, 82 and 86.

Cardiac signals are also applied to the inputs of an analog-to-digital (A/D) data acquisition system 90. The data acquisition system 90 is configured to acquire intracardiac electrogram signals, convert the raw analog data into a digital signal, and store the digital signals for later processing and/or telemetric transmission to an external IMD 10. The data acquisition system 90 samples cardiac signals across any pair of desired electrodes. The data acquisition system 90 may be coupled to the microcontroller 60, or other detection circuitry, for detecting an evoked response from the heart 12 in response to an applied stimulus, thereby aiding in the detection of "capture." Capture occurs when an electrical stimulus applied to the heart is of sufficient energy to depolarize the cardiac tissue, thereby causing the heart muscle to contract.

The microcontroller 60 is further coupled to a memory 94 by a suitable data/address bus 96. The memory 94 stores programmable operating, impedance measurements, impedance derivation and therapy-related parameters used by the microcontroller 60. The operating and therapy-related parameters define, for example, pacing pulse amplitude, pulse duration, electrode polarity, rate, sensitivity, automatic features, arrhythmia detection criteria, and the amplitude, wave shape and vector of each stimulating pulse to be delivered to the patient's heart 12 within each respective tier of therapy.

The impedance derivation parameters may include information designating i) sensing electrodes to use to define active sensing vectors, ii) sets and subsets of sensing vectors to use to monitor various regions of the heart, iii) sets or subsets of active sensing vectors to combine to form each pseudo sensing vector, iv) weight valves to use with active sensing vectors to form each pseudo sensing vector, v) algorithms for how to mathematically combine active sensing vectors to form each pseudo sensing vector, and the like.

The operating and therapy-related parameters may be non-invasively programmed into the memory 94 through a telemetry circuit 100 in telemetric communication with the external IMD 10, such as a programmer, trans-telephonic transceiver, or a diagnostic system analyzer. The telemetry circuit 100 is activated by the microcontroller 60 by a control signal. The telemetry circuit 100 advantageously allows intracardiac electrograms and status information relating to the operation of the IMD 10 (as contained in the microcontroller 60 or memory 94) to be sent to the external device 101 through an established communication link 103.

The microcontroller 60 includes an impedance derivation module 77 that derives impedances associated with pseudo sensing vectors based on impedance measurements along active sensing vectors. The impedance derivation module 77 performs the operations discussed herein in connection with FIG. 6.

The stimulation IMD 10 may include a physiologic sensor 107 to adjust pacing stimulation rate according to the exercise state of the patient. The physiological sensor 107 may further be used to detect changes in cardiac output, changes in the physiological condition of the heart, or diurnal changes in activity (e.g., detecting sleep and wake states). The battery 111 provides operating power to all of the circuits shown in FIG. 9.

The microcontroller 60 further controls a shocking circuit 117 by way of a control signal. The shocking circuit 117 generates stimulating pulses of low (up to 0.5 Joules), moderate (0.5-10 Joules), or high energy (11 to 40 Joules), as controlled by the microcontroller 60. Stimulating pulses are applied to the patient's heart 12 through at least two shocking electrodes, and as shown in this embodiment, selected from the left atrial (LA) coil electrode 28, the RV coil electrode 36, the SVC coil electrode 38 and/or the housing 40.

Figure 10:
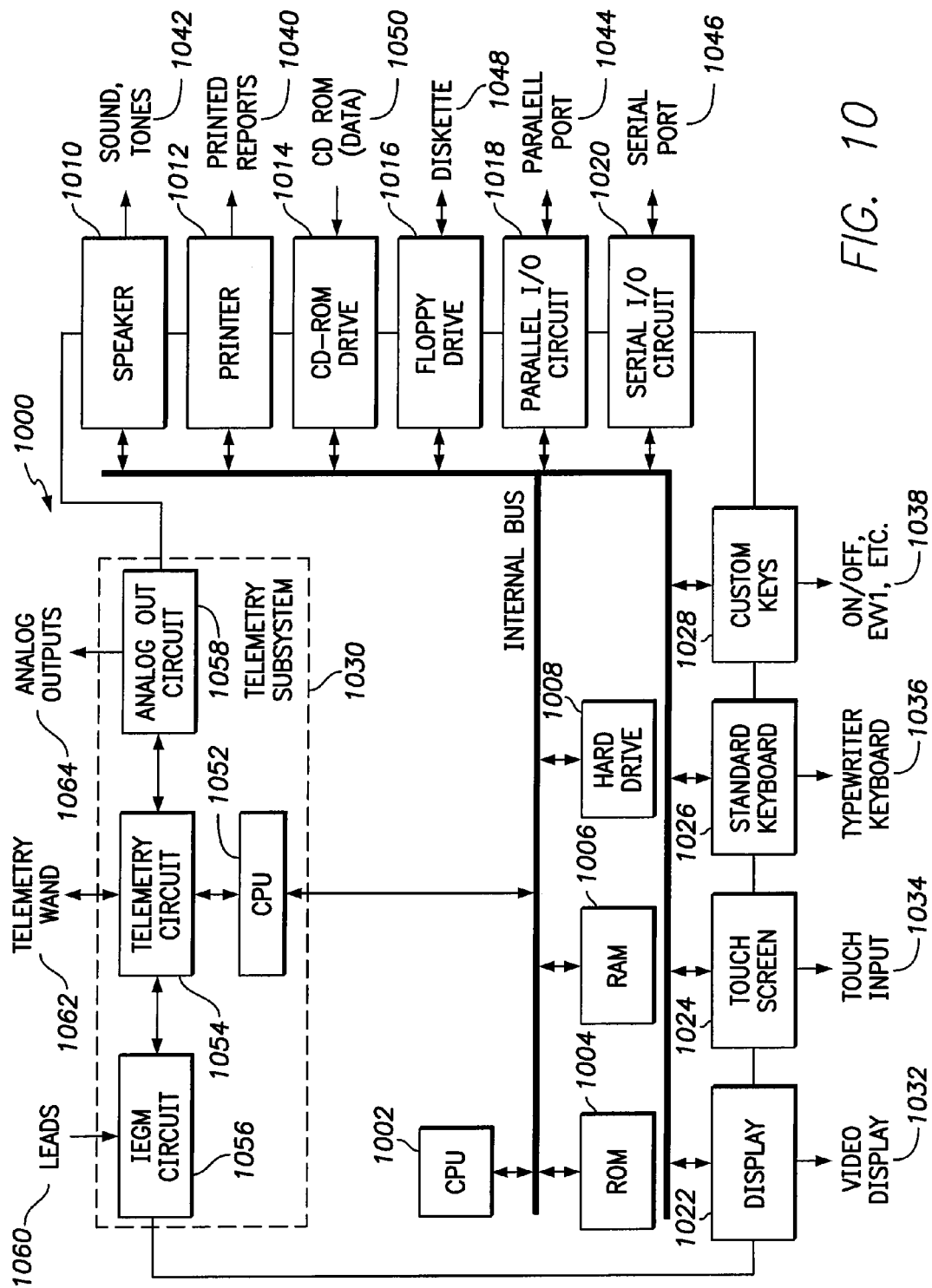
FIG. 10 illustrates a functional block diagram of the external device that is operated in accordance with the processes described herein and to interface with implantable medical devices as described herein.

FIG. 10 illustrates a functional block diagram of the external device 1000 that is operated in accordance with the processes described herein and to interface with implantable medical devices as described herein. The external device 1000 is configured to perform all or a portion of the operations described herein in connection with FIGS. 1-9. For example, the external device may perform all or a portion of the operations in FIGS. 1B and 6. For example, the external device 1000 may include all or a portion of the modules in the microcontroller 60 described in connect with FIG. 9. For example, the external device 1000 may include inputs to collect cardiac signals and DI data, as well as one or more of a CS module, DI module, MC module, therapy module, configured to perform the operations described in connection with FIG. 9.

The external device 1000 may be a workstation, a portable computer, an IMD programmer, a PDA, a cell phone and the like. The external device 1000 includes an internal bus that connects/interfaces with a Central Processing Unit (CPU) 1002, ROM 1004, RAM 1006, a hard drive 1008, the speaker 1010, a printer 1012, a CD-ROM drive 1014, a floppy drive 1016, a parallel I/O circuit 1018, a serial I/O circuit 1020, the display 1022, a touch screen 1024, a standard keyboard connection 1026, custom keys 1028, and a telemetry subsystem 1030. The internal bus is an address/data bus that transfers information between the various components described herein. The hard drive 1008 may store operational programs as well as data, such as waveform templates and detection thresholds.

The CPU 1002 typically includes a microprocessor, a microcontroller, or equivalent control circuitry, designed specifically to control interfacing with the external device 1000 and with the IMD 100. The CPU 1002 performs the COI measurement process discussed above. The CPU 1002 may include RAM or ROM memory, logic and timing circuitry, state machine circuitry, and I/O circuitry to interface with the IMD 100. The display 1022 (e.g., may be connected to the video display 1032). The touch screen 1024 may display graphic information relating to the IMD 100. The display 1022 displays various information related to the processes described herein. The touch screen 1024 accepts a user's touch input 1034 when selections are made. The keyboard 1026 (e.g., a typewriter keyboard 1036) allows the user to enter data to the displayed fields, as well as interface with the telemetry subsystem 1030. Furthermore, custom keys 1028 turn on/off 1038 (e.g., EVVI) the external device 1000. The printer 1012 prints copies of reports 1040 for a physician to review or to be placed in a patient file, and speaker 1010 provides an audible warning (e.g., sounds and tones 1042) to the user. The parallel I/O circuit 1018 interfaces with a parallel port 1044. The serial I/O circuit 1020 interfaces with a serial port 1046. The floppy drive 1016 accepts diskettes 1048. Optionally, the floppy drive 1016 may include a USB port or other interface capable of communicating with a USB device such as a memory stick. The CD-ROM drive 1014 accepts CD ROMs 1050.

The telemetry subsystem 1030 includes a central processing unit (CPU) 1052 in electrical communication with a telemetry circuit 1054, which communicates with both an IEGM circuit 1056 and an analog out circuit 1058. The circuit 1056 may be connected to leads 1060. The circuit 1056 is also connected to the implantable leads 114, 116 and 118 to receive and process IEGM cardiac signals as discussed above. Optionally, the IEGM cardiac signals sensed by the leads 114, 116 and 118 may be collected by the IMD 100 and then transmitted, to the external device 1000, wirelessly to the telemetry subsystem 1030 input.

The telemetry circuit 1054 is connected to a telemetry wand 1062. The analog out circuit 1058 includes communication circuits to communicate with analog outputs 1064. The external device 1000 may wirelessly communicate with the IMD 100 and utilize protocols, such as Bluetooth, GSM, infrared wireless LANs, HIPERLAN, 3G, satellite, as well as circuit and packet data protocols, and the like. Alternatively, a hard-wired connection may be used to connect the external device 1000 to the IMD 100.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the invention without departing from its scope. While the dimensions, types of materials and coatings described herein are intended to define the parameters of the invention, they are by no means limiting and are exemplary embodiments. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. §112, sixth paragraph, unless and until such claim limitations expressly use the phrase "means for" followed by a statement of function void of further structure.

What is claimed is:

1. A method for characterizing cardiac function, comprising:
    coupling an implantable electrode to a processing circuitry to collect cardiac signals associated with electrical or mechanical behavior of a heart over at least one cardiac cycle;
    applying a cardiac signal (CS) module to identify a timing feature of interest (FOI) from the cardiac signals;
    applying a dynamic impedance (DI) module to collect DI data over at least one cardiac cycle (CC), designated by the timing FOI, along at least one of i) a venous return (VR) vector or ii) a right ventricular function (RVF) vector;
    analyzing at least one morphologic characteristic from the DI data based on at least one of i) a VR-DI correlation metric to obtain a VR indicator associated with the CC or ii) a RVF-DI correlation metric to obtain a RVF indicator associated with CC.

2. The method of claim 1, further comprising, over multiple cardiac cycles, modulating at least one IMD therapy parameter and repeating the collecting and identifying operations to obtain a collection of at least one of VR indicators or RVF indicators associated with different IMD therapy parameters.

3. The method of claim 2, further comprising adjusting an IMD therapy configuration based on at least one of i) the collection of VR indicators and the VR-DI correlation metric such that the IMD operates to encourage a select VR level or ii) the collection of RVF indicators and the RVF-DI correlation metric such that the IMD operates to encourage a select RVF level.

4. The method of claim 2, further comprising determining a select level for the at least one IMD therapy parameter that provides at least one of i) a select peak to peak amplitude, ii) a select minimum amplitude, iii) a select DI change per unit time (dZ/dt), iv) a select slope, v) a select ventricular filling time, or vi) a select ventricular emptying time, of the DI data when plotted over time.

5. The method of claim 1, wherein the collecting of DI data includes utilizing an IMD case electrode and at least one of an SVC electrode, an IVC electrode and an RA electrode to define the VR vector and to collect the DI data.

6. The method of claim 1, wherein the analyzing includes determining, as the morphologic characteristic, at least one of i) a peak to peak (P-P) amplitude, ii) a minimum amplitude, iii) a minimum DI change per unit time (dZ/dt), iv) slope, v) a select ventricular filling time, or vi) a select ventricular emptying time, of the DI data over the CC.

7. The method of claim 5, wherein the VR-DI correlation metric represents a correlation between a mean pulmonary arterial pressure (mean PAP) and at least one of i) the P-P amplitude, ii) the minimum amplitude or iii) the dZ/dt.

8. The method of claim 5, wherein the VR-DI correlation metric represents at least one of i) a relation between changes in the P-P amplitude and changes in stroke volume and contractile strength, and ii) a relation between changes in the slope of the DI data and changes in direction and degree of cardiac contractility.

9. The method of claim 1, further comprising aligning the VR vector such that changes in the DI data substantially correlate with changes in stroke volume, end ventricular diastolic pressure, and mean pulmonary arterial pressure (mean PAP) for at least a portion of a duration of fluid loading and unloading.

10. The method of claim 1, wherein the VR vector extends through at least one of the SVC, RA or IVC.

11. The method of claim 1, wherein the RVF vector extends through at least a portion of the right ventricle.

12. The method of claim 1, wherein the DI data is collected and analyzed in connection with a select activity state and a select posture position of a patient.

13. A system for characterizing cardiac function, comprising:
an implantable electrode;
inputs configured to collect cardiac signals from the implantable electrode, the inputs associated with electrical or mechanical behavior of a heart over at least one cardiac cycle (CC);
a CS module configured to identify a timing feature of interest (FOI) from the cardiac signals;
a DI module configured to collect dynamic impedance (DI) data over at least one cardiac cycle (CC), designated by the timing FOI, along at least one of i) a venous return (VR) vector or ii) a right ventricular function (RVF) vector; and
a morphology characteristic (MC) module configured to analyze at least one morphologic characteristic from the DI data based on at least one of i) a VR-DI correlation metric to obtain a VR indicator associated with the CC or ii) a RVF-DI correlation metric to obtain a RVF indicator associated with CC.

14. The system of claim 13, further comprising a therapy module configured to modulate, over multiple cardiac cycles, at least one therapy parameter while the system obtains a collection of at least one of VR indicators or RVF indicators associated with different therapy parameters.

15. The system of claim 13, further comprising a therapy module configured to adjust a therapy configuration based on at least one of i) the collection of VR indicators and the VR-DI correlation metric such that the system operates to encourage a select VR level or ii) the collection of RVF indicators and the RVF-DI correlation metric such that the system operates to encourage a select RVF level.

16. The system of claim 13, wherein the MC module is further configured to determine a select level for the at least one therapy parameter that provides at least one of i) a select peak to peak amplitude, ii) a select minimum amplitude, iii) a select DI change per unit time (dZ/dt), iv) a select slope, v) a select ventricular filling time, or vi) a select ventricular emptying time, of the DI data when plotted over time.

17. The system of claim 13, further wherein the inputs are configured to collect the DI data utilizing an IMD case electrode and at least one of an SVC electrode, an IVC electrode and an RA electrode to define the VR vector.

18. The system of claim 13, wherein the MC module is configured to determine, as the morphologic characteristic, at least one of i) a peak to peak (P-P) amplitude, ii) a minimum amplitude, iii) a minimum DI change per unit time (dZ/dt), iv) slope, v) a select ventricular filling time, or vi) a select ventricular emptying time, of the DI data over the CC.

19. The system of claim 13, wherein the VR-DI correlation metric represents a correlation between a mean pulmonary arterial pressure (mean PAP) and at least one of i) the P-P amplitude, ii) the minimum amplitude or iii) the dZ/dt.

20. The system of claim 13, wherein the VR-DI correlation metric represents at least one of i) a relation between changes in the P-P amplitude and changes in stroke volume and contractile strength, and ii) a relation between changes in the slope of the DI data and changes in direction and degree of cardiac contractility.

21. The system of claim 13, wherein the VR vector is aligning such that changes in the DI data substantially correlate with changes in stroke volume, end ventricular diastolic pressure, and mean pulmonary arterial pressure (mean PAP) for at least a portion of a duration of fluid loading and unloading.

22. The system of claim 13, wherein the MC module collects and analyzes the DI data in connection with a select activity state and a select posture position of a patient.

* * * * *